US007850948B2

(12) United States Patent
Friebe et al.

(10) Patent No.: US 7,850,948 B2
(45) Date of Patent: *Dec. 14, 2010

(54) RADIOHALOGENATED BENZAMIDE DERIVATIVES AND THEIR USE IN TUMOR DIAGNOSIS AND TUMOR THERAPY

(75) Inventors: Matthias Friebe, Berlin (DE); Peter Muschick, Bernau/OT Ladeburg (DE); Andreas Huth, Berlin (DE)

(73) Assignee: Bayer Schering Pharma AG, Berlin (DE)

(*) Notice: Subject to any disclaimer, the term of this patent is extended or adjusted under 35 U.S.C. 154(b) by 0 days.

This patent is subject to a terminal disclaimer.

(21) Appl. No.: 12/207,774

(22) Filed: Sep. 10, 2008

(65) Prior Publication Data

US 2009/0012090 A1 Jan. 8, 2009

Related U.S. Application Data

(62) Division of application No. 11/076,023, filed on Mar. 10, 2005, now Pat. No. 7,427,390.

(60) Provisional application No. 60/551,356, filed on Mar. 10, 2004.

(30) Foreign Application Priority Data

Mar. 10, 2004 (DE) .................. 10 2004 011 720

(51) Int. Cl.
*A61K 51/00* (2006.01)
*A61M 36/14* (2006.01)
(52) U.S. Cl. .................. 424/1.89; 424/1.11; 424/1.65; 424/1.81; 424/1.85; 424/9.1
(58) Field of Classification Search ............... 424/1.11, 424/1.65, 1.81, 1.85, 1.89, 9.1, 9.3, 9.4, 9.5, 424/9.6, 9.7, 9.8; 514/613, 743, 747, 751
See application file for complete search history.

(56) References Cited

U.S. PATENT DOCUMENTS

| 6,448,277 B2 | 9/2002 | Altmann et al. |
| 6,818,661 B2 | 11/2004 | Seidelmann et al. |
| 6,878,720 B2 | 4/2005 | Altmann et al. |
| 7,002,022 B2 | 2/2006 | Altmann et al. |
| 7,012,081 B2 | 3/2006 | Krueger et al. |
| 7,081,468 B2 | 7/2006 | Krueger et al. |
| 7,122,547 B1 | 10/2006 | Huth et al. |
| 7,427,390 B2 * | 9/2008 | Friebe et al. ............... 424/1.89 |

OTHER PUBLICATIONS

Radioiodinated N-(2-Diethylaminoethyl)benzamide Derivatives with High Melanoma Uptake: Structure-Affinity Relationships, Metabolic Fate, and Intracellular Localization, Michael Eisenhut et al. pp. 3913-3922, J. Med. Chem. 2000.

* cited by examiner

*Primary Examiner*—D L Jones
(74) *Attorney, Agent, or Firm*—Millen, White, Zelano & Branigan, P.C.

(57) ABSTRACT

This invention relates to new radiohalogenated benzamide derivatives and their use in tumor diagnosis and tumor therapy. The radiohalogenated benzamide derivatives according to the invention exhibit novel and especially advantageous properties, in particular with respect to tumor concentration and retardation, liver concentration and blood accumulation. The radiation-therapy doses to be achieved in the tumor, compared to healthy body tissue, are advantageous for the compounds according to the invention.

19 Claims, No Drawings

RADIOHALOGENATED BENZAMIDE DERIVATIVES AND THEIR USE IN TUMOR DIAGNOSIS AND TUMOR THERAPY

This application is a divisional application of U.S. application Ser. No. 11/076,023, filed Mar. 10, 2005, which is now U.S. Pat. No. 7,427,390, and claims the benefit of the filing date of U.S. Provisional Application Ser. No. 60/551,356 filed Mar. 10, 2004, which are incorporated by reference herein.

This invention relates to new radiohalogenated benzamide derivatives and their use in tumor diagnosis and tumor therapy. The radiohalogenated benzamide derivatives according to the invention have novel and especially advantageous properties, in particular with respect to tumor concentration and retardation, liver concentration and blood accumulation.

BACKGROUND OF THE INVENTION

Radiodiagnostic agents and radiopharmaceutical agents play a decisive role in the diagnosis and combating of cancers. The tendency of many cancers to form metastases places high requirements on the efficiency specifically of radiodiagnostic agents as a serious tool for early detection of all metastases. This early detection of affected tissues in the body has a significant influence on the indicated therapy process. As a special example in this case, the extremely aggressive metastasis formation in malignant melanomas can be mentioned.

The early location of metastases is of special importance for the treatment of melanoma that grows aggressively. The lesions that are identified by means of computer tomography (x-ray radiation) generally require an invasive histological examination, however.

In this connection, nuclear-medicine research has developed a number of compounds that emit positrons and photons that accumulate after intravenous injection because of their property as metabolic substrate or bond to tumor-specific target structures in the primary tumor and in evacuated melanoma metastases. The graphic visualization of the activity distribution and the possible concentrations in the tumors are then performed with a positron-emission-tomography (PET) camera or a gamma camera, associated anatomically, evaluated and documented. As a gold standard of radioactive diagnostic agents, [F-18]2-fluoro-deoxyglucose (FDG) is now used for PET diagnosis (D. Delbeke et al., J. Nucl. Med. 40: 591-603 (1999); D. J. Macfarlane et al. J. Clin. Olncol. 16: 1770-1776 (1998); J. Ruhlmann et al. J. Nudl. Med. 40: 20P(1999). The absence of a suitable therapeutically relevant isotope pair represents a general drawback of [F-18]-labeled compounds. [F-18]2-Fluoro-deoxyglucose (FDG) can therefore be used exclusively for diagnosis.

It is specifically in the treatment of melanomas, because of early and aggressive metastasizing behavior, that only a very short survival period can be expected, especially in the case of patients in stages III and IV (see NIH Consensus Development Panel on Early Diagnosis and Treatment of Early Melanoma, J. Am. Med. Assoc. 268: 1314-1319 (1992); D. S. Rigel et al. CA Cancer J. Clin. 50: 215-236 (2000)). All approaches to a treatment with chemotherapeutic agents (Dacarbazin® by itself or Dartmouth protocol, etc.), immunotherapy (Interferon-Alpha, etc.) and gene therapy are not very successful to date. Operative removal of the metastases is the means of choice, but it often cannot be applied in the case of attacks of several organs. The use of a specific marker for melanomas, which can be provided with a diagnostic/therapeutic isotope pair and can be used for systemic treatment of multiple metastases, is therefore of great interest.

Such isotope pairs were for example 1-123 or 1-124 (diagnosis) and 1-125 or 1-131 (therapy), In addition, In-111/Y-86/Tc-99m (diagnosis) and Y-90/Re-186/Re-188 (therapy) can be mentioned.

The discovery that various radioiodinated benzamides have an affinity relative to melanocytes resulted in the development of various N-(2-dialkylaminoalkyl)-4-iodobenzamide derivatives (J. M. Michelot et al.: J. Nucl. Med. 32: 17573-1580 (1991) and U.S. Pat. No. 5,190,741), which were also tested clinically for the diagnosis of melanoma in a Phase II Study (J. M. Michelot et al.: J. Nucl. Med. 34: 1260-1266 (1993)). The described results show considerably improved absolute images relative to the use of simple radiolabeled amino acids such as iodo-thyrosine (for example, G. Kloss et al. Eur. J. Nucl. Med. 4: 179-186 (1979)). Compared to radioiodinated antibodies, more advantageous melanoma background properties would be achieved (cf. S. M. Larson et al. J. Nucl. Med. 32: 2887-291 (1991); G. L. Buraggi et al. Cancer Res. 45: 3378-3385 (1985)). Nevertheless, the latter with a 123-I-labeled compound for clinical use has disadvantageous properties especially with respect to the therapeutic application. The retardation in the tumor and the maximum concentration should be improved.

In addition, high background concentration of the compound leads to low-contrast visualization primarily in internal organs compared to extremities or to the head.

EP 0 317 873 B1 describes additional radioiodinated benzamides and their use as radiodiagnostic agents, thus, for example, 123-I—(S)—N-[(1-ethyl-2-pyrrolidinylmethyl]-5-iodo-2-methoxybenzamide.

By the introduction of polar groups on the phenyl radicals of the radiohalogenated benzamide derivatives, it has been possible to reduce these drawbacks (B. Bubeck, M. Eisenhut, A. Mohammed, C. Nicholl DE 195 19 508.6-41), but the problem continues to exist that the cited radioiodinated benzamides should be improved for therapeutic applications with respect to higher tumor accumulation and extended retardation.

The attempt to achieve the radiolabeling of benzamide derivatives by means of Tc-99m radio metal labeling and thus to use an economical isotope that is available through a generator resulted in compounds with considerably reduced melanoma accumulation (U. Titsch et al. J. Labelled Compds. Radiopharm, 40: 416-418 (1997); P. Auzeloux et al. J. Med. Chem. 43: 190-198 (2000). The substitution of the aromatic ring in the benzamide derivatives by a quadratic-pyramidal "3+1-" or amine-amide-dithiol-metal core while preserving the diethylamino-ethylene fragment resulted in a considerable improvement in the melanoma image (M. Friebe et al. J. Med. Chem. 43: 2745-2752 (2000); M. Friebe et al. J. Med. Chem. 44: 3132-3140 (2001); M. Eisenhut et al. J. Med. Chem. 45: 5802-5805 (2002)), but does not come up to the standard of the benzamide derivatives that are described below.

In J. Med. Chem. 2000, 43(21), 3913-22, DE 196 32 052 and Eisenhut et al. described, i.a., two benzamides named "BA40" and "BA42" with extraordinarily high concentration in the C57BL6-B16/Ft mouse model. In their publication, Eisenhut et al. describe the liver concentration of BA42, as the "best" compound, as the possible drawback of this compound especially for therapeutic applications. Another critical point is the blood accumulation of this compound with respect to the red bone marrow, which can result in limitations in the application for radiotherapy.

It is therefore an object of this invention to provide a radiopharmaceutical agent for the diagnosis and treatment of tumors, especially melanomas, whose affinity for tumor tissue is sufficiently high and that ensures a maximum "therapeutic window" (amount of radioactivity in tumor versus non-tumor) by sufficiently quick elimination from the remainder of the body. In this case, special attention is to be placed on tumor concentration and retardation, liver concentration and blood accumulation.

This object is achieved according to the invention by the provision of benzamide derivatives that have similar structural elements to the known, highly specific and highly sensitive radiohalogenated benzamide derivatives and can be used as complex ligands for transition metals. These radiohalogenated benzamide derivatives according to the invention have general formula (I)

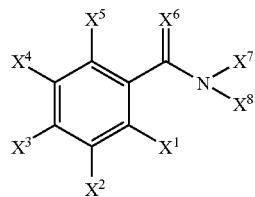

in which radicals $X^1$ to $X^5$, independently of one another, in each case represent a halogen, hydrogen, a radical of formula —$NR^1R^2$, an ether of formula —O—$R^3$, a branched or unbranched $C_1$-$C_{10}$ alkyl group, egg $C_1$, $C_2$, $C_3$, $C_4$, $C_5$, $C_6$, $C_7$, $C_8$, $C_9$, or $C_{10}$ alkyl group, a branched or unbranched $C_2$-$C_{10}$ alkenyl group, e.g. $C_1$, $C_2$, $C_3$, $C_4$, $C_5$, $C_6$, $C_7$, $C_8$, $C_9$, or $C_{10}$ alkenyl group, or an aryl or heteroaryl group that optionally can be substituted in each case by halogen or low alkoxy, whereby two adjacent radicals $X^1$ to $X^5$ can form a 5- to 7-membered ring, whereby one or more carbon atoms of the ring can be replaced by heteroatoms such as N, O or S, and radical $X^6$ is an oxygen or =NH, and radicals $X^7$ and $X^8$ can be the same or different and are hydrogen, substituted or unsubstituted $C_{1-12}$ alkyl, e.g. $C_1$, $C_2$, $C_3$, $C_4$, $C_5$, $C_6$, $C_7$, $C_8$, $C_9$, $C_{10}$, $C_{11}$ or $C_{12}$ alkyl, in particular methyl, ethyl, n-propyl, iso-propyl, n-butyl, iso-butyl, sec-butyl, tert-butyl, pentyl, hexyl, heptyl, substituted or unsubstituted $C_{2-12}$ alkenyl, e.g. $C_2$, $C_3$, $C_4$, $C_5$, $C_6$, $C_7$, $C_8$, $C_9$, $C_{10}$, $C_{11}$ or $C_{12}$ alkenyl, in particular ethenyl, propenyl, butenyl, pentenyl, hexenyl, heptenyl, substituted or unsubstituted $C_{3-6}$ cycloalkyl, e.g. $C_3$, $C_4$, $C_5$, or $C_6$ cycloalkyl, substituted or unsubstituted $C_{3-6}$ cycloalkenyl, e.g. $C_3$, $C_4$, $C_5$, or $C_6$ cycloalkenyl, substituted or unsubstituted $C_{2-6}$ carbalkoxyalkyl, e.g. $C_2$, $C_3$, $C_4$, $C_5$, or $C_6$ carbalkoxyalkyl, substituted or unsubstituted $C_{2-6}$ carbalkoxyalkenyl, e.g. $C_2$, $C_3$, $C_4$, $C_5$, or $C_6$ carbalkoxyalkenyl, —$C_{1-12}$alkyl$NR^8R^9$, e.g. $C_1$, $C_2$, $C_3$, $C_4$, $C_5$, $C_6$, $C_7$, $C_8$, $C_9$, $C_{10}$, $C_{11}$ or $C_{12}$ alkyl$NR^8R^9$ in particular-methyl$NR^8R^9$, -ethyl$NR^8R^9$, -propyl$NR^8R^9$, or substituted or unsubstituted $C_{6-12}$ aryl or heteroaryl; in each case optionally substituted in one or more places by —$OR^4$, —$COOR^5$, —$CONR^6R^7$, cyano, halogen or —$NR^8R^9$; or $X^7$ and $X^8$ together form a 5- to 7-membered ring, whereby one or more carbons of the ring can be replaced by heteroatoms, such as N, O or S, whereby $R^1$ and $R^2$ are the same or different and are hydrogen, $C_{1-12}$ alkyl, e.g. $C_1$, $C_2$, $C_3$, $C_4$, $C_5$, $C_6$, $C_7$, $C_8$, $C_9$, $C_{10}$, $C_{11}$ or $C_{12}$ alkyl, in particular methyl, ethyl, propyl, butyl, pentyl, hexyl, heptyl, $C_{2-12}$ alkenyl, e.g. $C_2$, $C_3$, $C_4$, $C_5$, $C_6$, $C_7$, $C_8$, $C_9$, $C_{10}$, $C_{11}$ or $C_{12}$ alkenyl, in particular ethenyl, propenyl, butenyl, pentenyl, hexenyl, heptenyl, $C_{3-6}$ cycloalkyl, e.g. $C_3$, $C_4$, $C_5$ or $C_6$ cycloalkyl, $C_{3-6}$ cycloalkenyl, e.g. $C_3$, $C_4$, $C_5$, or $C_6$ cycloalkenyl, $C_{2-6}$ carboxyalkyl, e.g. $C_2$, $C_3$, $C_4$, $C_5$, or $C_6$ carbalkoxyalkyl, $C_{2-6}$ carboxyalkenyl, e.g. $C_2$, $C_3$, $C_4$, $C_5$, or $C_6$ carbalkoxyalkenyl, $C_{6-12}$ arylsulfonyl, e.g. $C_6$, $C_7$, $C_8$, $C_9$, $C_{10}$, $C_{11}$, or $C_{12}$ arylsulfonyl, carboxyaryl, in particular 07-13 carboxyaryl, e.g. $C_7$, $C_8$, $C_9$, $C_{10}$, $C_{11}$, $C_{12}$, or $C_{13}$ carboxyaryl, or carboxyheteroaryl, in particular $C_{7-13}$ carboxyheteroaryl, e.g. $C_7$, $C_8$, $C_9$, $C_{10}$, $C_{11}$, $C_{12}$ or $C_{13}$ carboxyheteroaryl, wherein the carboxyheteroaryl preferably comprises 1, 2, 3, 4, 5 or 6 hetero atoms selected from the group S, N, or O; in each case optionally substituted in one or more places, e.g. 1, 2, 3, 4 or 5 substitutions, by preferably aryl, heteroaryl, $OR^4$, $COOR^5$, $CONR^6R^7$, cyano, halogen, $NR^8R^9$, or two substituents, preferably adjacent substituents taken together form a 3, 4, 5, 6, 7 or 8 membered ring optionally with 1, 2, 3, or 4 hetero atoms, e.g. selected from O, S, or N, provided that $R^1$ and $R^2$ cannot simultaneously be hydrogen, $R^3$ is hydrogen, $C_{6-12}$ aryl, heteroaryl, $C_{1-10}$ alkyl, e.g. $C_1$, $C_2$, $C_3$, $C_4$, $C_5$, $C_6$, $C_7$, $C_8$, $C_9$, or $C_{10}$, alkyl, in particular methyl, ethyl, propyl, iso-propyl, n-butyl, iso-butyl, tert-butyl, pentyl, hexyl, heptyl, $C_{2-10}$ alkenyl, e.g. $C_2$, $C_3$, $C_4$, $C_5$, $C_6$, $C_7$, $C_8$, $C_9$, or $C_{10}$, alkenyl, in particular ethenyl, propenyl, butenyl, pentenyl, hexenyl, heptenyl, $C_{2-10}$ alkynyl, e.g. $C_2$, $C_3$, $C_4$, $C_5$, $C_6$, $C_7$, $C_8$, $C_9$, or $C_{10}$ alkynyl, in particular ethynyl, propynyl, butynyl, pentynyl, hexynyl, heptynyl, $C_{3-6}$ cycloalkyl, e.g. $C_3$, $C_4$, $C_5$, or $C_6$ cycloalkyl, $C_{3-6}$ cycloalkenyl, e.g. $C_3$, $C_4$, $C_5$, or $C_6$ cycloalkenyl; in each case optionally substituted in one or more places preferably by $OR^4$, $COOR^5$, $CONR^6R^7$ (whereby polyethers, such as, e.g., C—O—C≡C—O—C—R, are possible, since an O-alkyl group can be substituted by O-alkyl), cyano, halogen or $NR^8R^9$, $R^4$ and $R^5$ are the same or different and are hydrogen, $C_{1-12}$ allyl, e.g. $C_1$, $C_2$, $C_3$, $C_4$, $C_5$, $C_6$, $C_7$, $C_8$, $C_9$, $C_{10}$, $C_{11}$ or $C_{12}$ alkyl, in particular methyl, ethyl, propyl, butyl, pentyl, hexyl, heptyl, $C_{2-12}$ alkenyl, e.g. $C_2$, $C_3$, $C_4$, $C_5$, $C_6$, $C_7$, $C_8$, $C_9$, $C_{10}$, $C_{11}$ or $C_{12}$ alkenyl, in particular ethenyl, propenyl, butenyl, pentenyl, hexenyl, heptenyl, $C_3$-(cycloalkyl, e.g. $C_3$, $C_4$, $C_5$, or $C_6$ cycloalkenyl, $C_{3-6}$ cycloalkenyl, e.g. $C_3$, $C_4$, $C_5$, or $C_6$ cycloalkenyl; in each case optionally substituted in one or more places preferably by aryl, heteroaryl, $OR^{10}$, $COOR^{11}$, $CONR^6R^7$, cyano, halogen or $NR^8R^9$, $R^6$, $R^7$, $R^8$ and $R^9$ are the same or different and are hydrogen, $C_{1-12}$ alkyl, e.g. $C_1$, $C_2$, $C_3$, $C_4$, $C_5$, $C_6$, $C_7$, $C_8$, $C_9$, $C_{10}$, $C_{11}$ or $C_{12}$ alkyl, in particular methyl, ethyl, propyl, iso-propyl, n-butyl, iso-butyl, tert-butyl, pentyl, hexyl, heptyl, $C_{2-12}$alkenyl, e.g. $C_2$, $C_3$, $C_4$, $C_5$, $C_6$, $C_7$, $C_8$, $C_9$, $C_{10}$, $C_{11}$ or $C_{12}$ alkenyl, in particular ethenyl, propenyl, butenyl, pentenyl, hexenyl, heptenyl, $C_{3-6}$ cycloalkyl, e.g. $C_3$, $C_4$, $C_5$, or $C_6$ cycloalkyl, $C_{3-6}$ cycloalkenyl, e.g. $C_3$, $C_4$, $C_5$, or $C_6$ cycloalkenyl, in each case optionally substituted in one or more places by preferably $OR^4$, or $R^6$ and $R^7$ or $R^8$ and $R^9$ in each case together form a 5- to 7-membered ring, whereby one or more carbons of the ring can be replaced by heteroatoms such as N, O or S, and $R^{10}$, $R^{11}$ are the same or different and can be hydrogen, $C_{1-12}$ alkyl, e.g. $C_1$, $C_2$, $C_3$, $C_4$, $C_5$, $C_6$, $C_7$, $C_8$, $C_9$, $C_{10}$, $C_{11}$, or $C_{12}$ alkyl, in particular methyl, ethyl, propyl, iso-propyl, n-butyl, iso-butyl, tert-butyl, pentyl, hexyl, heptyl, $C_{2-12}$ alkenyl, e.g. $C_2$, $C_3$, $C_4$, $C_5$, $C_6$, $C_7$, $C_8$, $C_9$, $C_{10}$, $C_{11}$ or $C_{12}$ alkenyl, in particular ethenyl, propenyl, butenyl, pentenyl, hexenyl, heptenyl, $C_{3-6}$ cycloalkyl, e.g. $C_3$, $C_4$, $C_5$, or $C_6$ cycloalkyl, or $C_{3-6}$ cycloalkenyl, e.g. $C_3$, $C_4$, $C_5$, or $C_6$ cycloakenyl; which optionally can be substituted in each case in one or more places preferably by aryl, heteroaryl, $OR^4$, $COOR^5$, $CONR^6R^7$, cyano, halogen, or $NR^8R^9$, provided that at least one of radicals $X^1$ to $X^5$, preferably $X^4$ is a radioactive halogen, at least one of radicals $X^1$ to $X^5$, preferably $X^1$ is an ether —O—$R^3$, at least one of radicals $X^1$ to $X^5$, preferably $X^3$ is a radical of formula —$NR^1R^2$, in which either $R^1$ or $R^2$ is a substituted or unsubstituted radical carboxyalkyl, in particular $C_{2-6}$ carboxyalkyl, e.g. $C_2$, $C_3$, $C_4$, $C_5$ or $C_6$ carboxyalkyl, carboxyalkenyl, in particular $C_{2-6}$ carboxyalkenyl, e.g. $C_2$, $C_3$, $C_4$, $C_5$ or $C_6$ carboxyalkenyl, carboxy aryl, in particular $C_{7-13}$ carboxyaryl, e.g. $C_7$, $C_8$, $C_9$, $C_{10}$, $C_{11}$, $C_{12}$ or $C_{13}$ carboxyaryl, or carboxyheteroaryl, in particular $C_7$-$C_{13}$ carboxy heteroaryl, e.g. $C_7$, $C_8$, $C_9$, $C_{10}$, $C_{11}$, $C_{12}$ or $C_{13}$ carboxy heteroaryl; in each case optionally substituted in one or more places, e.g. 1, 2, 3, 4 or 5 substitutions, preferably by aryl, heteroaryl, $OR^4$, $COOR^5$, $CONR^6R^7$, cyano, halogen, $NR^8R^9$, or two substituents, preferably adjacent substituents taken together form a 3, 4, 5, 6, 7 or 8 membered ring optionally with 1, 2, 3, or 4 hetero atoms, e.g. selected from O, S, or N; preferably a carboxyalkyl, in particular $C_{2-6}$ carboxyalkyl or carboxyaryl, in particular $C_{7-13}$ carboxyaryl; in each case optionally substituted with one or more substituents from the group of halogen, e.g. F, Cl, Br or I, or —O—$R^4$ or two substituents, preferably adjacent substituents, taken together from a 3, 4, 5, 6, 7 or 8 membered ring, optionally with 1, 2, 3 or 4 hetero atoms, e.g. O, N, or S; more preferably substituted or unsubstituted $C_7$ carboxyaryl, e.g. benzo-carbonyl, in particular halogen-benzo carbonyl, e.g. 1-fluoro-benzo-4-carbonyl, or 1-chloro-benzo-4-carbonyl, alkoxy-benzo-carbonyl, e.g. 1-methoxy-benzo-4-carbonyl, benzo-carbonyl or benzo-[1,3]dioxole-5-carbonyl; and that if $X^1$ is methoxy and $X^6$ is O, $X^8$ is hydrogen and $X^7$ is $NH(CH_2)_2Net_2$, and $X^4$ means $I^{131}$, $X^3$ is not NHAc, and physiologically compatible salts thereof.

Especially in reference to the therapeutic use of the compounds according to the invention, it has been shown that the blood accumulation of the compounds may be a critical point. It is very important that the compound which is labeled with the radio-active isotope is excreted from the blood as fast as possible. The compounds according to the invention and especially the compounds BA52 (see Formula (IIa)) or BA91; BA 93; BA95 and BA100 (Formula IIb-e), respectively show, surprisingly enough, considerably less blood accumulation than the closest prior art (compound of Eisenhut et al. with NH—Ac as substitution in the ring). This reduced blood concentration is advantageous with respect to the bone marrow toxicity.

In addition, the liver kinetics of the compounds according to the invention is much better than the liver kinetics of the most similar compound in the prior art. In particular, the final result was very surprising. It had been expected that the compounds according to the invention and in particular BA52 are more lipophilic by the substitution, and thus have a stronger protein bond (higher and longer accumulation in the blood) and, in addition, are metabolized more greatly via the liver. Compound 52 indeed has a higher lipophilicity but does advantageously not fulfill this expectation.

Another drawback of the most similar compounds of the prior art is that the compounds of Eisenhut et al. dehalogenate more quickly in the body than the compounds according to the invention. This is shown by the fact that in the compound according to the invention, the thyroid gland accumulation, produced by iodine released from the compound (the intact compound does not accumulate in the thyroid gland tissue) is lower.

Surprisingly enough, compounds according to the invention, in particular BA52, BA 93, BA95 and BA 100 show an extended retardation in the melanoma tissue, which should mean an enlargement of the therapeutic window in the patient in connection with the previously named properties. The retardation over an extended period of time leads to an enhanced tumor dose. Therefore, the extended retardation in the melanoma tissue is more important than the initial tumor uptake (after 1 h).

In terms of structure, the compounds according to the invention are distinguished by the substitution in the aromatic amino group by carboxy alkyl, carboxy alkenyl, carboxy aromatic or carboxy heteroaromatic compounds with the formation of an amide bond.

As mentioned above, Eisenhut et al. have produced, i.e. two benzamides (BA40) and (BA42) which show extraordinarily high concentration in the C57BL6-B16/F1 mouse model. The tumor concentration of the compound BA52 according to the invention is comparable in this model, but the retention of BA52 in the tumor is considerably longer. This observation is even more striking in the NMRI-SK-Me13 human xenograft mouse model. BA 40 is completely washed out of the tumor after 72 hours. In contrast thereto, BA 52 is still accumulated with at least 13% of the injected dose per gram tissue of the tumor after 96 hours.

In their publication, Eisenhut et al. describe the liver concentration of BA42, which is considered the "best" compound, as a possible drawback of this compound especially for therapeutic applications. The liver concentration of the substances according to the invention, in particular BA52, BA 91, BA93, BA95 and BA100, e.g., after 6 and 24 hours, is considerably lower (see Table 1). It is of importance that the compounds according to the present invention are excreted from the liver considerably faster than BA40 and BA42 although the initial accumulation in the liver is comparable. Another critical point is the blood accumulation of this compound, which can result in limitations in the application for radiotherapy. The BA52 according to the invention also shows here a considerably lower blood accumulation after 6 and 24 hours, respectively, (see Table 1) which leads to a remarkably lower radio-active dose to the bone marrow (lower side effects).

In addition, the radioisotope 1-131 seems to be more stable in the compounds according to the invention and in particular bonded to BA52, BA91, BA93, BA95 and BA 100. The thyroid gland accumulation of BA40 and BA42, an indication of dehalogenation in vivo, is increased by a factor of 10-15 compared to the compounds according to the invention.

The fact that despite higher lipophilicity, BA52 shows a lower blood accumulation in the mouse model (Table 1) is also advantageous. This was not predictable because of the usually higher blood plasma binding of more lipophilic substances. Also, more lipophilic substances are more likely metabolized by the liver such that a lower accumulation was not to be expected after 5 or 24 hours.

TABLE 1

Tissue Concentration of Radioiodinated Benzamides in the C57BL6-B16/F1 Mouse Model, n = 3

| Organ | Comparison Substance BA40' | | | Comparison Substance BA42' | | | BA52 | | |
|---|---|---|---|---|---|---|---|---|---|
| | 1 hour | 6 hours | 24 hours | 1 hour | 6 hours | 24 hours | 1 hour | 5 hours | 24 hours |
| Tumor | 16.61* | 16.48 | 8.02 | 21.87 | 23.32 | 16.06 | 14.83 | 22.69 | 18.82 |
| Blood | 2.32 | 1.86 | 0.19 | 3.30 | 2.56 | 0.21 | 1.46 | 0.69 | 0.05 |
| Liver | 11.32 | 9.61 | 4.54 | 8.03 | 9.86 | 3.72 | 19.11 | 6.53 | 0.49 |

| Organ | BA91 | | | BA93 | | | BA95 | | |
|---|---|---|---|---|---|---|---|---|---|
| | 1 h | 6 h | 24 h | 1 h | 6 h | 24 h | 1 h | 5 h | 24 h |
| Tumor | 9.68 | 16.72 | 13.83 | 10.73 | 21.67 | 23.46 | 17.45 | 14.83 | 29.69 |
| Blood | 1.06 | 0.97 | 0.22 | 1.30 | 0.82 | 0.22 | 1.26 | 0.76 | 0.07 |
| Liver | 12.68 | 3.63 | 0.76 | 13.71 | 5.81 | 1.18 | 16.35 | 8.54 | 0.75 |

| | BA100 | | |
|---|---|---|---|
| Organ | 1 h | 6 h | 24 h |
| Tumor | 25.51 | 28.10 | 31.66 |
| Blood | 1.21 | 0.70 | 0.07 |
| Liver | 15.49 | 4.64 | 0.76 |

*% Injected Dose (ID)/g of Tissue
'Value from Eisenhut et al. J. Med. Chem. 2000, 43(21), 3913-22

Based on this organ distribution data in mice, dosimetry calculations were conducted. To this end, the "Medical Internal Radiation Dose" (MIRD) process was used (M. G. Stabin et al. J Nucl Med, 37; 538-546 (1996); R. Loevinger et al. Society of Nuclear Medicine, 1988, NY; J. A. Siegel et al. J Nucl Med 35: 152-156 (1994); J. A. Siegel et al. J Nucl Med 40: 37S-61S (1999); G. Sgouros et al. J Nucl Med 34: 689-694 (1993); M. S. Muthluswainy et al. J Nucl Med 39: 1243-1247 (1998)). This process is based on a spherical model and calculates the radiation dose deposited in the tumor and the organs of the corresponding species as a function of the radioisotope that is used, the distribution of the compound in the body and the amount of radioactive compound administered (Table 2). Thus, estimates can be conducted for the "therapeutic window" of the compound as well as regarding expected side effects. A high dose value (mGy/MBq) in the tumor is advantageous while as low a value as possible for blood and organs produces a low radiation dose (side effect). Since the blood and organ dose determine the maximum dose that can be administered, compounds with low organ/blood doses and high tumor dose have the larger "therapeutic window."

TABLE 2

Dose quotient mGy/MBq for benzamide derivatives. Calculated for defined organs based on tumor and organ distribution experiments in the syngenic C5BL6-B16 mouse tumor model. MIRDOSE 3.1, 1995, Stabin et al. was used for calculation. The areas under the curve (residence times) on which the calculation is based were calculated with SigmaPlot 8.02, SPSF, Inc.

| Dose/Organ | Comparison Substance BA40' mGy/MBq | Comparison Substance BA42' mGy/MBq | BA52 mGy/mBq |
|---|---|---|---|
| Tumor (1 g) | 507 | 1256 | 4870 |
| Blood | 35 | 47 | 4 |
| Bone marrow | 13 | 17 | 1 |
| Liver | 332 | 324 | 92 |

'Tumor and organ distribution data were taken from Eisenhut et al. J. Med. Chem. 2000, 43(21), 3913-22. The organ weights were normalized to standard mouse values.

According to the invention, a radiohalogenated benzamide derivative of this invention is preferred, whereby the halogen isotope is selected from F-18, Br-76, I-123, I-124, I-125, I-131 and At-211.

Further preferred is a radiohalogenated benzamide derivative of this invention, whereby the halogen isotope [I-131] is iodine, whose specific activity is between 10 mCi/mg and 1500 mCi/mg (non HPLC purified), preferably between 100 mCi/mg and 800 mCi/mg (non HPLC purified). If the compound is purified by HPLC or alike methods, the specific radioactivity will be determined by the specific activity of the isotope batch used and will be higher. Processes for determination of the specific activity are known to one skilled in the art and can be taken from relevant textbooks and/or scientific publications, such as, e.g., Wessels, B. W., Meares, C. F. Physical and Chemical Properties of Radionuclide Therapy. Semin Radiat Oncol. 2000 April; 10(2):115-22, and the references cited therein.

Still more preferred is a radiohalogenated benzamide derivative of this invention, whereby radical $X^6$ is an oxygen. As an alternative, radical $X^6$ can be an =NH group.

Also more preferred is a radiohalogenated benzamide derivative of this invention, whereby one of radicals $X^7$ and $X^8$ is a hydrogen.

Also more preferred is a radiohalogenated benzamide derivative of this invention, whereby one of radicals $X^7$ and $X^8$ is a hydrogen, while the other radical $X^7$ or $X^8$ is $C_1$-$C_{12}$ alkyl, substituted with an amine —$NR^8R^9$. It is particularly preferred that, if one of the radicals $X^7$ and $X^8$ is hydrogen that the other radical $X^7$ or $X^8$ is $C_2$, $C_3$ or $C_4$ alkyl, substituted, preferably terminally with an amine —$NR^8R^9$, e.g. —$CH_2NR^8R^9$, —$CH_2CH_2NR^8R^9$, —$CH_2CH_2CH_2NR^8R^9$.

Even more preferred is a radiohalogenated benzamide derivative of this invention, whereby $R^8$ and $R^9$ are $C_2H_5$ or form a 5- or 6-membered ring, whereby one or more carbon atoms of the ring can be replaced by heteroatoms, such as N, O or S. $R^8$ and $R^9$ preferably have this preferred meaning when one of radicals $X^7$ and Xs is hydrogen and the other radical $X^7$ or $X^8$ is $C_2$, $C_3$ or $C_4$ alkyl, substituted, preferably terminally with an amine $NR^8R^9$, e.g. —$CH_2NR^8R^9$, —$CH_2CH_2NR^8R^9$, —$CH_2CH_2CH_2NR^8R^9$. In this context $R^8$ and $R^9$ preferably have the meaning substituted or unsubstituted methyl, ethyl, propyl or butyl.

Still more preferred is a radiohalogenated benzamide derivative of this invention, whereby one of radicals $X^1$ to $X^5$ represents a radical —$NR^1R^2$.

Also more preferred is a radiohalogenated benzamide derivative of this invention, whereby $R^1$ is a carboxyaryl group, and l is a hydrogen. Still more preferred is a radiohalogenated benzamide derivative of this invention, whereby $R^1$ is a $C_2$-$C_6$ carboxyalkyl or $C_2$-$C_6$ carboxyalkenyl, and $R^2$ is a hydrogen. Especially preferred are arylcarboxyl substituents on $R^1$.

Still more preferred is a radiohalogenated benzamide derivative of this invention, whereby $X^1$ is selected from —O—$R^3$, in particular from an —O—$CH_3$ group, an O—$C_2H_5$ group, an —O—$C_2H_5$O—$CH_3$ group or an —O—$C_2H_5$—OH group.

A further preferred radio halogenated benzamide derivative of this invention, whereby $X^3$ is a radical of formula —$NR^1R^2$ in which $R^1$ or $R^2$ is a substituted or unsubstituted radical carboxyalkyl, in particular $C_{2-6}$ carboxyalkyl, carboxyalkenyl, in particular $C_{2-6}$ carboxyalkenyl, carboxyaryl, in particular $C_{7-13}$ carboxyaryl, or carboxyheteroaryl, in particular $C_{7-13}$ carboxyheteroaryl; more preferably a carboxyalkyl, in particular $C_{2-6}$ carboxyalkyl or carboxyaryl, in particular $C_{7-13}$ carboxyaryl, optionally substituted with 1, 2, 3, 4, or 5 halogen(s), e.g. F, Cl, Br, or I, —O—$R^4$, wherein $R^3$ preferably has the meaning $C_{1-6}$ alkyl, or two substituents, preferably adjacent substituents, taken together form a 3, 4, 5, 6 or 7 or 8 membered ring, optionally with 1, 2, 3 or 4 hetero atoms, e.g. N, O, or S; in particular preferred embodiments $R^1$ is a $C_7$ carboxyaryl, e.g. benzo-carbonyl, optionally substituted with halogen, e.g. F, Cl, Br or I, —O—$R^4$ or two substituents taken together form a 5, 6 or 7 membered ring, preferably comprising 1 or 2 hetero atoms, e.g. O, N or S, preferably in this case and the preceding preferred embodiments $R^2$ is hydrogen. It is even more preferred, that the $C_7$ carboxyaryl is selected from the group consisting of monohalogen substituted benzo-carbonyl, in particular 1-fluoro-benzo-4-carbonyl or 1-chloro-benzo-4-carbonyl, mono substituted alkoxy-benzo-carbony, in particular 1-methoxy-benzo-carbonyl, benzo-carbonyl or benzo[1,3]dioxole-5-carbonyl.

Also more preferred is a radiohalogenated benzamide derivative of this invention, whereby $X^1$ is an —O—$R^3$, wherein $R^3$ is preferably $C_{1-10}$ alkyl, e.g. $C_1$, $C_2$, $C_3$, $C_4$, $C_5$, $C_6$, $C_7$, $C_8$, $C_9$, or $C_{10}$, alkyl, in particular methyl, ethyl, propyl, iso-propyl, n-butyl, iso-butyl, tert-butyl, pentyl, hexyl, heptyl, $C_{2-10}$ alkenyl, e.g. $C_2$, $C_3$, $C_4$, $C_5$, $C_6$, $C_7$, $C_8$, $C_9$, or $C_{10}$, alkenyl, in particular ethenyl, propenyl, butenyl, pentenyl, hexenyl, heptenyl, in particular a —O—$CH_3$, —O—$C_2H_5$, —O—$C_2H_5$—O—$CH_3$ group, $X^4$ is a halogen, in particular [123] iodine, [125] iodine or [131] iodine, and $X^3$ is a radical —$NR^1R^2$, in which $R^1$ is substituted or unsubstituted carboxyalkyl, in particular $C_{2-6}$ carboxyalkyl, carboxyalkenyl, in particular $C_{2-6}$ carboxyalkenyl, carboxy aryl, in particular, $C_{7-13}$ carboxyaryl, or carboxyheteroaryl, in particular $C_7$-$C_{13}$ carboxy heteroaryl, in particular an aryl-carboxylic acid group and $R^2$ is a hydrogen. In a particular preferred embodiment $X^1$ can be an —O—$CH_3$ group, $X^4$ is a halogen, in particular [123] iodine, [125] iodine or [131] iodine, and $X^3$ is a radical —$NR^1R^2$, in which $R^1$ is a benzo [1,3]dioxole-5-carbonyl group, a substituted or unsubstituted benzo-carbonyl group, a 1-chloro-benzo-4-carbonyl group, 1-methoxy-benzo-4-carbonyl group, or a 1-fluoro-benzo-4-carbonyl group, and $R^2$ is a hydrogen.

In an alternative preferred embodiment $X^1$ can be an —O—$C_2H_5$ group, $X^4$ is a halogen, in particular [123] iodine, [125] iodine, or [131] iodine, and $X^4$ is a radical —$NR^1R^2$, in which $R^1$ is substituted or unsubstituted carboxyalkyl, in particular $C_{2-6}$ carboxyalkyl, carboxyalkenyl, in particular $C_{2-6}$ carboxyalkenyl, carboxyaryl, in particular, $C_{7-13}$ carboxyaryl, in particular a benzo[1,3]dioxole-5-carbonyl group, a substituted or unsubstituted benzo-carbonyl group, a 1-chloro-benzo-4-carbonyl group, a 1-methody-benzo-4-carbonyl group, or a 1-fluoro-benzo-4-carbonyl group, or carboxyheteroaryl, in particular $C_7$-$C_{13}$ carboxy heteroaryl, and $R^2$ is a hydrogen.

In an alternative preferred embodiment $X^1$ can be an —O—$C_2H_5$—O—$CH_3$ group, $X^4$ can be [123] iodine, [125] iodine or [131] iodine, and $X^3$ can be a radical —$NR^1R^2$, in which $R^1$ is a benzo[1,3]dioxole-5-carbonyl group, a substituted or unsubstituted benzo-carbonyl group, a 1-chloro-benzo-4-carbonyl group, a 1-methoxy-benzo-4-carbonyl group, or a 1-fluoro-benzo-4-carbonyl group, and $R^2$ is a hydrogen.

As an alternative, $X^1$ can be an —O—$C_2H_5$—OH group, $X^4$ can be [123] iodine, [125] iodine, or [131] iodine, and $X^3$ can be a radical $NR^1R^2$, in which $R^1$ is a substituted or unsubstituted carboxyalkyl, in particular $C_{2-6}$ carboxyalkyl, carboxyalkenyl, in particular $C_{2-6}$ carboxyalkenyl, carboxy aryl, in particular, $C_{7-13}$ carboxyaryl, in particular benzo[1,3]dioxole-5-carbonyl group, or a substituted or unsubstituted benzo-carbonyl group, a 1-chloro-benzo-4-carbonyl group, a 1-methoxy-benzo-4-carbonyl group, or a 1-fluoro-benzo-4-carbonyl group, carboxyheteroaryl, in particular $C_7$-$C_{13}$ carboxy heteroaryl, and $R^2$ is a hydrogen. It is particularly preferred that in this context $X^6$ is an oxygen. It is in this context also preferred that $X^2$ and $X^5$ are hydrogen.

Likewise preferred is a radiohalogenated benzamide derivative of this invention, whereby at least one of radicals $X^1$ to $X^5$ is a radical —$NR^1R^2$, whereby $R^1$ is a carboxyalkyl group, and $R^2$ is a hydrogen, and one of radicals $X^1$ to $X^5$ is an O—$R^3$ group, $X^6$ is an =NH group, and one of radicals $X^1$ to $X^5$ is a halogen, in particular [123] iodine, [125] iodine or [131] iodine.

Also preferred is a radiohalogenated benzamide derivative of this invention, whereby at least one of radicals $X^1$ to Xs is a radical —$NR^1R^2$, whereby $R^1$ is a carboxyalkyl group, and $R^2$ is a hydrogen, and one of radicals $X^1$ to $X^5$ represents an —O—$CH_3$ group, $X^6$ represents an =NH group, and one of radicals $X^1$ to $X^5$ represents a halogen, in particular [123] iodine, [125] iodine or [131] iodine.

According to a particularly preferred aspect of this invention, a radiohalogenated benzamide derivative of this invention of Formula IIa.

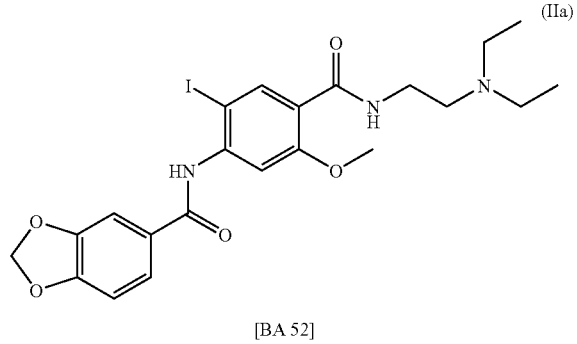

[BA 52]

and pharmaceutical acceptable salts thereof are made available.

According to another particularly preferred aspect of this invention, further radiohalogenated benzamide derivatives of this invention of Formula IIb to e and pharmaceutical acceptable salts thereof are made available.

(IIb-IIe)

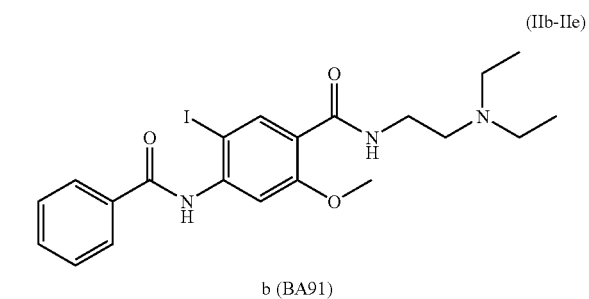

b (BA91)

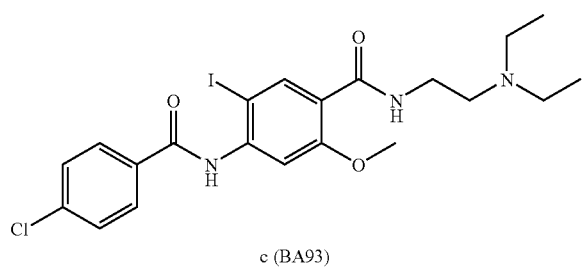

c (BA93)

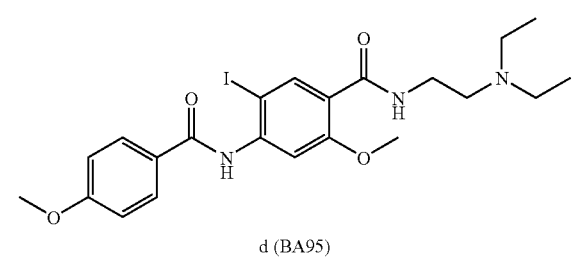

d (BA95)

-continued

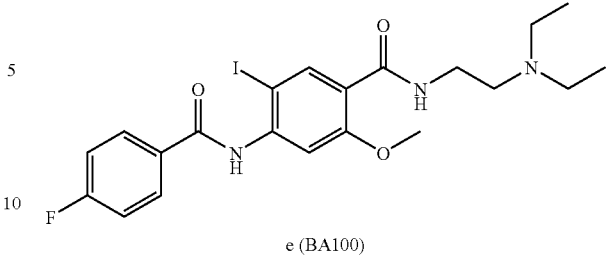

e (BA100)

Another aspect of this invention relates to a process for the production of a pharmaceutical composition for the diagnosis or treatment of tumors, in particular malignant melanoma, including the mixing of a radiohalogenated benzamide derivative of this invention with a suitable pharmaceutical vehicle. These vehicles can be selected from phosphate-buffered physiological common salt solution, physiological common salt solution, water, mixtures that consist of the previously named solutions/solvents with ethanol, dimethyl sulfoxide, Tween®, meglumine, etc.

Preferred is a pharmaceutical composition of this invention, whereby the halogen isotope is selected from F-18, Br-75, I-123, I-124, I-125, I-131 or At-211.

More preferred is a pharmaceutical composition of this invention, whereby the halogen isotope is [1-131] iodine, whose specific activity is between 10 mCi/mg and 1500 mCi/mg (non HPLC purified), preferably between 100 mCi/mg and 800 mCi/mg (non HPLC purified). If the compound is purified by HPLC or alike methods, the specific radioactivity will be determined by the specific activity of the isotope batch used and will be higher.

Still another aspect of this invention then relates to the use of a radiohalogenated benzamide derivative of this invention for the production of a preparation for the diagnosis and treatment of tumors, in particular melanomas. In this case, the compound can be used either with a diagnostically relevant radioisotope such as I-123 for a Single Photon Emission Computed Tomography (SPECT) study or with F-18/I-124/Br-76-labeled benzamide derivative for the PET. For a therapeutic application, the benzamide derivative can be labeled with I-131/I-125/At-211 and can be used for systemic radiotherapy as well as for local, intratumoral therapy.

In this case, I-131-labeled benzamide represents a special case, since both the β'-radiation portion can be used therapeutically and the accompanying γ-emission can be used diagnostically (SPECT). An advantage of the halogen-labeled compounds could consequently exist in the development of a compound with an isotope, in which a low dosage is used for diagnostic imaging and then after dosimetric tolerance calculation, a therapeutically relevant, higher radioactive dose is administered.

Within the scope of this invention, "alkyl" is defined in each case as a straight-chain or branched alkyl radical, such as, for example, methyl, ethyl, propyl, isopropyl, butyl, isobutyl, sec-butyl, pentyl, isopentyl or hexyl, heptyl, octyl, nonyl, decyl, undecyl, or dodecyl.

Within the scope of this invention, "alkoxy" is defined in each case as a straight-chain or branched alkoxy radical, such as, for example, methyloxy, ethyloxy, propyloxy, isopropyloxy, butyloxy, isobutyloxy, sec-butyloxy, pentyloxy, isopentyloxy, hexyloxy, heptyloxy, octyloxy, nonyloxy, decyloxy, undecyloxy or dodecyloxy.

Within the scope of this invention, "cycloalkyl" is defined as monocyclic alkyl rings, such as cyclopropyl, cyclobutyl, cyclopentyl, cyclohexyl or cycloheptyl, cyclooctyl, cyclononyl or cyclododecyl, but also bicyclic rings.

Within the scope of this invention, "cycloalkenyl" is defined as monocyclic alkenyl rings, such as cyclopropenyl, cyclobutenyl, cyclopentenyl, cyclohexenyl or cycloheptenyl, cyclooctenyl, cyclononenyl or cyclodecenyl, but also bicyclic rings.

Within the scope of this invention, "halogen" is defined in each case as fluorine, chlorine, bromine, or iodine. "Radiohalogen" is defined in each case as F-18, Br-75, I-123, I-124, I-125, I-131 or At-211.

Within the scope of this invention, "alkenyl" is defined in each case as a straight-chain or branched alkenyl radical, which contains 2-6, preferably 2-4 C atoms. For example, the following radicals can be mentioned: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, but-3-en-1-yl and allyl.

The aryl radical comprises 3-12 carbon atoms in each case and can be benzocondensed in each case and/or further substituted. For example, there can be mentioned: phenyl, naphthyl, biphenyl, fluorenyl, anthracenyl, benzo[1,3]dioxole etc.

The heteroaryl radical comprises 3-16 ring atoms in each case, and, instead of carbon, can contain in the ring one or more heteroatoms that are the same or different, such as oxygen, nitrogen or sulfur, and can be monocyclic, bicyclic or tricyclic, and in addition can be benzocondensed in each case and/or further substituted.

There can be mentioned, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl, etc., and benzo derivatives thereof such as, e.g., benzofuranyl, benzothienyl, benzoxazolyl, benzimidazolyl, indazolyl, indolyl, isoindolyl, etc.; or pyridyl, pyridazinyl, pyrimidinyl, pyrazinyl, triazinyl, etc., and benzo derivatives thereof, such as, e.g., quinolyl, isoquinolyl, etc.; or azocinyl, indolizinyl, purinyl, etc., and benzo derivatives thereof; or quinolinyl, isoquinolinyl, cinnolinyl, phthalazinyl, quinazolinyl, quinoxalinyl, napththyridinyl, pteridinyl, carbazolyl, acridinyl, phenazinyl, phenothiazinyl, phenoxazinyl, xanthenyl, oxepinyl, etc.

If an acid group is included, the physiologically compatible salts of organic and inorganic bases are suitable as salts, such as, for example, the readily soluble alkali and alkaline-earth salts, as well as N-methyl-glucamine, dimethyl-glucamine, ethyl glucamine, lysine, 1,6-hexadiamine, ethanolamine, glucosamine, sarcosine, serinol, tris-hydroxy-methyl-aminomethane, aminopropanediol, Sovak Base, 1-amino-2,3,4-butane-triol.

If a basic group is included, the physiologically compatible salts of organic and inorganic acids are suitable, such as hydrochloric acid, sulfuric acid, phosphoric acid, citric acid, tartaric acid, fumaric acid, etc.

The compounds of general formula I according to the invention also contain possible tautomeric forms and comprise the E- or Z-isomers, or, if a chiral center is present, also the racemates and enantiomers.

The production of the compounds according to the invention can be carried out by a compound of formula III,

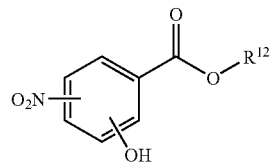

Formula III in which $R^{12}$ means hydrogen or low-alkyl, optionally esterified, etherified, amidated, the nitro group reduced, acylated and radiohalogenated, whereby the radiohalogenation is carried out virtually in one of the last stages, if possible in the last stage. However, a compound of formula IV

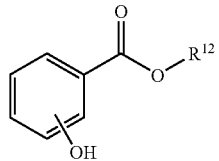

Formula IV in which $R^{12}$ means hydrogen or low-alkyl, can also be nitrated and then the process is continued as described above. Another possibility consists in a compound of formula V

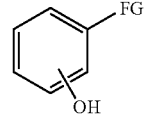

Formula V in which $R^{12}$ means hydrogen or low-alkyl, and FG means iodine, bromine, o-triflate, O-mesylate, O-tosylate or O-nonaflate, optionally esterified or amidated, etherified, carbonylated, nitrated, and then further processed as described above.

In the production of the compounds according to the invention, the amide formation is carried out according to methods that are known in the literature. A start can be made for amide formation from a corresponding ester. According to J. Org. Chem., 1995, 8414, the ester is reacted with, e.g., aluminum trimethyl and the corresponding amine in the solvents, such as toluene, at temperatures of 60° C. up to the boiling point of the solvent. If the molecule contains two ester groups, both are converted into the same amide.

For amide formation, however, all processes that are known from peptide chemistry are available. For example, the corresponding acid in aprotic, polar solvents, such as, for example, dimethylformamide, can be reacted with the amine via an activated acid derivative that can be obtained with, for example, hydroxybenzotriazole and a carbodiimide, such as, for example, diisopropylcarbodiimide or else with preformed reagents, such as, for example, HATU (Chem. Comm. 1994, 201) or BTU, at temperatures of between 0° C. and the boiling point of the solvent. For the amide formation, the process can also be used with the mixed acid anhydride, the acid chloride, the imidazolide or the azide. In reactions of acid chloride, dimethylacetamide can be used as a solvent at temperatures from room temperature up to the boiling point of the solvent, preferably at 80-100° C. The reaction, however, can also be performed in inert solvents, such as methylene chloride or tetrahydrofuran, with the addition of a base, such as, for example, triethylamine at temperatures of −10° C. up to the boiling point of the solvent. An addition of dimethylaminopyridine has frequently proven useful.

An acylation with acid anhydrides or acid chlorides frequently leads to bisacyl compounds that can be converted by treatment with bases, such as, for example, potassium hydroxide solution or potassium carbonate, into the monoacyl compounds. The same holds true for sulfonic acid chlorides. With acid anhydrides, a bisacylation by using acid anhydride in glacial acetic acid can be avoided.

If various amide groups are to be introduced into the molecule, for example, the second ester group must be introduced after the production of the first amide group in the molecule and then amidated, or there is a molecule in which one group is present as ester and the other is present as acid, and the two groups are amidated in succession according to various methods.

An esterification of acids is possible by reaction with trimethylsilyldiazomethane. The methyl ester is then obtained. The reaction is possible in solvents such as methanol or toluene, preferably in mixtures thereof. The temperature shifts between 0° C. and the boiling point of the solvent, and is preferably room temperature. An esterification of a carboxylic acid in addition to a phenol is also possible with alcoholic hydrochloric acid, preferably at the boiling point of the solvent.

The introduction of non-radiohalogens is carried out according to processes that are known in the literature, e.g., by reaction with bromine, N-bromine or N-chlorosuccinimide or urotropin hydrotribromide in polar solvents, such as tetrahydrofuran, acetonitrile, methylene chloride, glacial acetic acid or dimethylformamide.

The reduction of the nitro group is performed in polar solvents at room temperature or elevated temperature. As catalysts for the reduction, metals such as Raney nickel or noble-metal catalysts such as palladium or platinum, or else palladium hydroxide optionally on vehicles are suitable. Instead of hydrogen, for example, ammonium formate, cyclohexene or hydrazine can also be used in a known way. Reducing agents such as tin(II) chloride or titanium(III) chloride can also be used, such as complex metal hydrides optionally in the presence of heavy metal salts. As reducing agents, iron can also be used. The reaction is then performed in the presence of an acid, such as, e.g., acetic acid or ammonium chloride, optionally with the addition of a solvent, such as, for example, water, methanol, iron/ammonia, etc. In the case of extended reaction time, in this variant, an acylation of the amino group can occur.

If an alkylation of an amino group is desired, the amine can be subjected to a reductive alkylation with aldehydes or ketones, whereby it can be reacted in the presence of a reducing agent, such as, for example, sodium cyanoborohydride, in a suitable inert solvent, such as, for example, ethanol, at temperatures of 0° C. up to the boiling point of the solvent. If a start is made from a primary amino group, the reaction can optionally be performed in succession with two different carbonyl compounds, whereby mixed derivatives are obtained [literature, e.g., Verardo et al. Synthesis (1993), 121; Synthesis (1991), 447; Kawaguchi, Synthesis (1985), 701; Micovic et al. Synthesis (1991), 1043].

It may be advantageous to form the Schiff base first by reaction of the aldehyde with the amine in solvents such as ethanol or methanol, optionally with the addition of adjuvants such as glacial acetic acid, and then to add only reducing agents, such as, e.g., sodium cyanoborohydride.

The introduction of the alkenyl group is carried out with the corresponding vinyl compounds under the conditions of the Heck reaction. For the introduction of the ethinyl groups, the Sonogashira reaction is used, and for the introduction of the aryl or hetaryl radicals, the Suzuki reaction or the Still reaction is used.

As leaving groups, halogens such as fluorine, chlorine, bromine, iodine or O-mesylate, O-tosylate, O-triflate or O-nonaflate are suitable. The nucleophilic substitution for the introduction of ethinyl radicals or ethenyl radicals is performed under catalysis of transition metal complexes, such as Pd(O), e.g., palladium tetrakistriphenylphosphine, $Pd_2(dba)_3$ or $Pd(^{2+})$, such as palladium-bis-tri-o-tolylphosphine-dichloride, nickel(II) or nickel(0) according to methods that are known in the literature optionally in the presence of a base and optionally under co-catalysis of a salt, such as, for example, copper(I) iodide or lithium chloride.

As nucleophiles, for example, vinyl or ethinyl compounds, tin-organic compounds or zinc-organic compounds or boronic acids are suitable. The reaction can be performed in polar solvents such as dimethylformamide, dimethylacetamide, N-methylpyrrolidone, acetonitrile, in hydrocarbons such as toluene or in ethers such as tetrahydrofuran, dimethoxyethane or diethyl ether. As bases, inorganic bases such as alkali- or earth-alkali hydroxides or -bicarbonates, -carbonates, or -phosphates, or organic bases such as cyclic, alicyclic and aromatic amines, such as pyridine, triethylamine, DBU or Hünig base, are suitable, whereby in many cases, bases such as diethylamine or piperidine can also be solvents at the same time. The application of pressure may be necessary for the reaction. An addition of ligands, such as, for example, triphenylphosphine or xanthphos, can have a positive effect.

The substitution of leaving groups in aromatic compounds or heteroaromatic compounds by amides is carried out under catalysis, for example by palladium or copper catalysis. In the case of copper catalysis (literature, see Synlett. 2002, 427), solvents such as dioxane or dimethylformamide are used at temperatures up to the boiling point of the solvent, preferably 120° C. As a base, potassium phosphate or else cesium carbonate is used. Ethylenediamine is advantageous for complexing the copper(I) iodide that is used as a catalyst. An application of pressure is not harmful. In the case of palladium catalysis, both palladium(II) salts, such as palladium (IT) acetate, and palladium(0) complexes, such as palladium $(O)_2$dibenzylideneacetone$_3$ (literature, see JACS 2002, 6043, THL 1999, 2035, Org. Lett 2001, 2539, THL 2001, 4381 or THL 2001, 3681), can. As solvents, toluene, dioxane or dimethylformamide are used at temperatures from room temperature up to the boiling point of the solvent, preferably around 100° C. As a co-ligand, BINAP, DPPF or xanthphos is used. A base is also necessary. For this purpose, cesium carbonate, potassium phosphate or else sodium-t-butylate is used. These components can be combined in various ways.

The amide group can also be introduced by carbonylation, however. To this end, a start is made from the corresponding aromatic or heteroaromatic compounds with a leaving group (see above), which are reacted with carbon monoxide at normal pressure or else elevated pressure and an amine in the presence of transition metal catalysts, such as, for example, palladium(II) chloride or palladium(II) acetate, palladium tetrakistriphenylphosphine or in solvents, such as, for example, dimethylformamide. The addition of a ligand such as triphenylphosphine, and the addition of a base such as tributylamine may be advantageous (see, for example, J. org. Chem. 1974, 3327; J. org. Chem. 1996, 7482; Synth. Comm. 1997, 367; Tetr. Lett. 1998, 2835, J. org. Chem. 2003, 3558).

If various amide groups are to be introduced into the molecule, for example, the second ester group must be introduced into the molecule after the first amide group is produced and then amidated, or there is a molecule in which one group is present as an ester and the other is present as an acid, and the two groups are amidated in succession according to various methods.

Acid groups can also be introduced by carbonylation, however. To this end, a start is made from the corresponding aromatic or heteroaromatic compounds with a leaving group (see above), which are reacted with carbon monoxide at normal pressure or else elevated pressure in the presence of transition metal catalysts, such as, for example, palladium(II) chloride or palladium(II) acetate, palladium tetrakistriphenylphosphine, in solvents such as, for example, dimethylformamide, whereby water is added. A base such as, for example, triethylamine is necessary. In addition, ligands, such as, for example, triphenylphosphine or preferably (1,1'-bisphenylphosphino)ferrocene, are necessary. The pressure extends from room temperature to 50 bar, preferably 5-40 bar. The reaction can prolong an elevated temperature. It extends from room temperature up to the boiling point of the solvent, and preferably a temperature of 40-80° C. is used.

An alkylation of a phenol is possible by reaction with an alkylating agent such as, for example, alkyl halide, alkyl triflate, alkyl mesylate or alkyl tosylate in solvents such as dimethylformamide, N-methylpyrrolidone, or tetrahydrofuran in the presence of bases such as cesium carbonate, potassium carbonate or else DBU, DABCO. The phenolate can also be preformed, however, by the phenol being pretreated with bases such as sodium hydride at temperatures of 0-100° C., preferably at 50° C., and then the alkylating agent being added.

Alkylation can thus be achieved in that according to the Mitsunobu variant, reaction is done with an alcohol in the presence of for example, triphenylphosphine and azodicarboxylic acid ester.

The hydrogenation of alkene or alkine groups in the molecule is carried out in the usual way by, for example, catalytically activated hydrogen. As catalysts, heavy metals, such as palladium or platinum, optionally on a vehicle or Raney nickel, can be used. As solvents, alcohols, such as, e.g., ethanol, are suitable. The procedure is performed at temperatures of 0° C. up to the boiling point of the solvent and at pressures up to 20 bar, but preferably at room temperature and normal pressure. By the use of catalysts, such as, for example, a Lindlar catalyst triple bonds can be partially hydrogenated to double bonds, whereby preferably the Z-form is produced. This hydrogenation is preferably performed in pyridine as a solvent with palladium on calcium carbonate as a catalyst. In the same way, the Z-double bond can be produced from the triple bond by reduction with diimine, for example according to R. M. Moriatry et al. Synth. Comm. 17, 703, 1987.

Ether cleavages are performed according to processes that are common in the literature. In this case, a selective cleavage can also be achieved in several groups that are present in the molecule. In this case, the ether is treated with, for example, boron tribromide in solvents such as dichloromethane at temperatures of between −100° C. up to the boiling point of the solvent, preferably at −78° C. It is also possible, however, to cleave the ether by sodium thiomethylate in solvents such as dimethylformamide. The temperature can be between room temperature and the boiling point of the solvent, preferably at 150° C. In the case of benzyl ethers, the cleavage is also possible with strong acids, such as, for example, trifluoroacetic acid at temperatures from room temperature up to the boiling point.

For radioiodinated compounds, in principle several methods are suitable. In particular here, the Tl/trifluoroacetic acid/NaI method, the iodate/NaI method, the use of chloroamine-T™ or Jodogen™ can be mentioned (M. Eisenhut et al., Radioiodination Chemistry and Radioiodinated Compounds, in: Handbook of Nuclear Chemistry—Vol. 4, 257-278 A. Vértes, S, Nagy and Z. Klencsár (eds.) Kluver Academic Publishers (2003)).

When the Tl/trifluoroacetic acid/NaI method is used, the benzamide precursor is dissolved under an inert gas atmosphere in trifluoroacetic acid and mixed with Tl/trifluoroacetate)₃. After an incubation time, the NaI is added either in water, in dilute NaOH alkaline solution or dissolved in another suitable solvent. After stirring at room temperature or at an elevated temperature, the reaction of the precursor to form the desired product of general formula I results.

For radioiodination by the iodate/NaI method, the iodination precursor is dissolved in acid (preferably 1N hydrochloric acid), mixed with $KIO_3$ solution (preferably aqueous), and after the halide solution of the corresponding isotope is added at room temperature, it is reacted. The reaction is then suppressed by adding, for example, $Na_2S_2O_5$. The purification of the products that are produced can be carried out via normal-phase or reverse-phase chromatography.

The cleavage of the protective groups is carried out in a way that is known in the literature. Thus, a t-butyloxcarbonyl group can be removed by being reacted in a solvent such as tetrahydrofuran, dioxane or ethanol with an acid, such as, e.g., 1N hydrochloric acid at temperatures of between room temperature and the boiling point of the solvent. It is also possible to cleave the t-BOC group with strong acids such as trifluoroacetic acid at temperatures of between −20° C. and the boiling point, preferably at room temperature. A solvent such as methylene chloride is not absolutely necessary but may be advantageous. In the same way, t-butyl ester can be cleaved.

The reduction of a ketone takes place in a known way by a complex metal hydride, such as, for example, sodium borohydride or lithium borohydride, in solvents such as ethanol, tetrahydrofuran or diethyl ether at temperatures of 0° C. up to the boiling point of the solvent.

According to commonly used methods, such as, for example, crystallization, any form of chromatography or salt formation, the isomer mixtures can be separated into enantiomers or E/Z isomers.

The production of salts is carried out in the usual way, by a solution of the compound of formula I being mixed with the equivalent amount or an excess of a base or acid, which optionally is in solution, and the precipitate being separated or the solution being worked up in the usual way.

The invention is now to be further described below in the examples without being limited thereto.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

The examples below explain the production of the compounds according to the invention.

Example 1

4-Propionylamino-N-(2-diethylamino-ethyl)-2-methoxy-benzamide

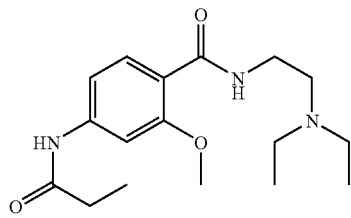

a.) 2-Hydroxy-4-nitro-benzoic acid methyl ester

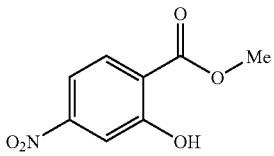

916 mg (5 mmol) of 2-hydroxy-4-nitro-benzoic acid is dissolved in a mixture that consists of 8 ml of methanol and 32 ml of toluene, and it is slowly mixed with a solution of trimethylsilyldiazomethane in hexane (2 molar). After the addition is completed, stirring is continued for 1.25 hours at room temperature. After the reaction mixture is concentrated by evaporation, 1 g (about 100% of theory) of 2-hydroxy-4-nitro-benzoic acid methyl ester is obtained.

b.) 2-Methoxy-4-nitro-benzoic acid methyl ester

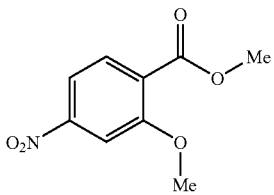

788 mg (4 mmol) of 2-hydroxy-4-nitro-benzoic acid methyl ester is mixed in 20 ml of absolute dimethylformamide with 177 mg of sodium hydride (60%; 4.4 mmol), and it is heated for 1 hour to 50° C. After cooling to room temperature, it is mixed with 625 mg (4.4 mmol) of methyl iodide and heated for 4 hours to a bath temperature of 80° C. After concentration by evaporation, it is taken up in 50 ml of water and extracted three times with 25 ml each of ethyl acetate. The ethyl acetate phase is washed with water, dried, filtered and concentrated by evaporation. The residue is chromatographed on 5 g of Isolute SI (50 μm) with a gradient from cyclohexane to cyclohexane:ethyl acetate=80:20 as an eluant, and 400 mg (47% of theory) of 2-methoxy-4-nitro-benzoic acid methyl ester is obtained as an oil.

Produced analogously are:
2-Ethoxy-4-nitro-benzoic acid methyl ester; 2-methoxyethoxy-4-nitro-benzoic acid methyl ester c.) 4-Nitro-N-(2-diethylamino-ethyl)-2-methoxy-benzamide

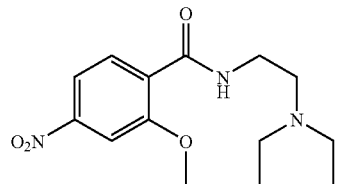

480 mg (2.27 mmol) of 2-methoxy-4-nitro-benzoic acid methyl ester is first mixed in 25 ml of toluene with 264 mg (0.32 ml; 2.27 mmol) of 2-N,N-diethylamino-ethylamine and then mixed quickly with 1.14 ml of trimethyl aluminum (2-molar in toluene). It is then heated for 2.25 hours to a bath temperature of 120° C. After cooling, it is mixed with 30 ml of dilute sodium bicarbonate solution and extracted three times with 25 ml each of ethyl acetate. The ethyl acetate phase is washed with water, dried, filtered and concentrated by evaporation. 300 mg (45% of theory) of 4-nitro-N-(2-diethylamino-ethyl)-2-methoxy-benzamide is obtained.

The same compound can also be produced from the commercially available 2-hydroxy-4-nitro-benzoic acid: 5 g (25.4 mmol) of 2-hydroxy-4-nitro-benzoic acid is heated in 12 ml of thionyl chloride for 2 hours to 100° C. It is then concentrated by evaporation in a vacuum and mixed twice with toluene and concentrated by evaporation. The residue is taken up in 40 ml of tetrahydrofuran, and while being cooled with ice, it is mixed first with 2.82 g (3.88 ml; 27.9 mmol) of triethylamine and then with 3.24 g (27.9 mmol; 3.92 ml) of 2-N,N-diethylaminoethylamine. It is stirred overnight at room temperature. Then, it is concentrated by evaporation, the residue is taken up in 100 ml of water and extracted three times with 100 ml each of ethyl acetate. The ethyl acetate phase is washed with water, dried, filtered and concentrated by evaporation. 7.4 g (98% of theory) of 4-nitro-N-(2-diethylamino-ethyl)-2-methoxy-benzamide (melting point: 59.3° C.) is obtained.

Produced analogously are: 4-nitro-N-(2-diethylamino-ethyl)-2-ethoxy-benzamide; 4-nitro-N-(2-diethylamino-ethyl)-2-methoxyethoxy-benzamide; 4-nitro-2-methoxy-N-(2-morpholin-4-yl-ethyl)-benzamide; 4-nitro-N-(2-diisopropylamino-ethyl)-2-ethoxy-benzamide; 4-nitro-N-(2-dibutylamino-ethyl)-2-ethoxy-benzamide; 4-nitro-2-methoxy-N-(2-thiomorpholin-1-yl-ethyl)-benzamide; 4-nitro-2-methoxy-N-(2-piperidin-1-yl-ethyl)-benzamide; 4-nitro-2-methoxy-N-(2-pyrrolidin-1-yl-ethyl)-benzamide.

d.) 4-Amino-N-(2-diethylamino-ethyl)-2-methoxy-benzamide

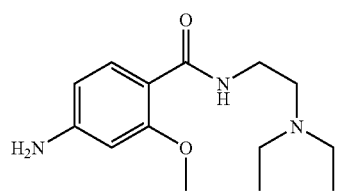

5.7 g (19.3 mmol) of 4-nitro-N-(2-diethylamino-ethyl)-2-methoxy-benzamide is dissolved in 120 ml of tetrahydrofuran:ethanol 1:1>mixed with 2 g of palladium on carbon (10%×50% water) and hydrogenated for 1 hour at room temperature and normal pressure. After being drawn off on diatomaceous earth and after concentration by evaporation, 5.45 g of 4-amino-N-(2-diethylamino-ethyl)-2-methoxy-benzamide is obtained.

Produced analogously are: 4-amino-N-(2-diethylaminoethyl)-2-ethoxy-benzamide; 4-amino-N-(2-diethylaminoethyl)-2-methoxyethoxy-benzamide; 4-amino-2-methoxy-N-(2-morpholin-4-yl-ethyl)-benzamide; 4-amino-N-(2-diisopropylamino-ethyl)-2-ethoxy-benzamide; 4-amino-N-(2-dibutylamino-ethyl)-2-ethoxy-benzamide; 4-amino-2-methoxy-N-(2-thiomorpholin-1-yl-ethyl)-benzamide; 4-amino-2-methoxy-N-(2-piperidin-1-yl-ethyl)-benzamide; 4-amino-2-methoxy-N-(2-pyrrolidin-1-yl-ethyl)-benzamide.

e.) 4-Propionylamino-N-(2-diethylamino-ethyl)-2-methoxy-benzamde

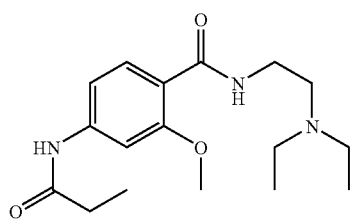

387 mg (1.46 mmol) of 4-amino-N-(2-diethylamino-ethyl)-2-methoxy-benzamide in 15 ml of dimethylformamide is mixed with 1.5 ml of propionic acid anhydride, and this mixture is stirred for 2 hours at room temperature. After concentration by evaporation in a vacuum, the residue is taken up in 40 ml of dilute sodium bicarbonate solution and then extracted with 40 ml of ethyl acetate. The ethyl acetate phase is washed with water, dried, filtered and concentrated by evaporation. The residue is absorptively precipitated with diisopropyl ether and suctioned off. 250 mg (55.7% of theory) of 4-propionylamino-N-(2-diethylamino-ethyl)-2-methoxy-benzamide (melting point 137° C.) is obtained.

Produced analogously are: 4-propionylamino-N-(2-diethylamino-ethyl)-2-ethoxy-benzamide; 4-propionylamino-N-(2-diethylamino-ethyl-2-methoxyethoxy-benzamide; 4-propionylamino-2-methoxy-N-(2-morpholin-4-yl-ethyl)-benzamide; 4-propionylamino-N-(2-diisopropylamino-ethyl)-2-ethoxy-benzamide; 4-propionylamino-N-(2-dibutylamino-ethyl)-2-ethoxy-benzamide; 4-propionylamino-2-methoxy-N-(2-thiomorpholin-1-yl-ethyl)-benzamide; 4-propionylamino-2-methoxy-N-(2-piperidin-1-yl-ethyl)-benzamide; 4-propionylamino-2-methoxy-N-(2-pyrrolidin-1-yl-ethyl)-benzamide Example 2

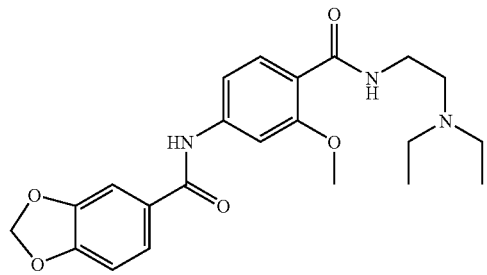

Benzo[1,3]-dioxole-5-carboxylic acid [4-(2-diethylamino-ethylcarbamoyl)-5-methoxy-phenyl]-amide 200 mg (0.75 mmol) of 4-amino-N-(2-diethylamino-ethyl)-2-methoxy-benzamide in 10 ml of chloroform is mixed with 5 ml of 3,4-methylenedioxybenzoic acid chloride (in chloroform) and this mixture is stirred for 3 hours at room temperature. After concentration by evaporation in a vacuum, the residue is taken up in 40 ml of dilute sodium bicarbonate solution and then extracted with 40 ml of methylene chloride. The methylene chloride phase is washed with water, dried, filtered and concentrated by evaporation. The crude product, 315 mg, is taken up in methylene chloride and purified on silica gel. As a mobile solvent, a mixture that consists of methylene chloride/methanol (977:3→90:10) is used. 210 mg (67% of theory) of benzo[1,3]dioxole-5-carboxylic acid [4-(2-diethylamino-ethylcarbamoyl)-5-methoxy-phenyl]-amide (melting point 131.1° C.) is obtained.

Produced analogously are: benzo[1,3]dioxole-5-carboxylic acid [4-(2-diethylaminoethylcarbamoyl)-5-ethoxy-phenyl]-amide; benzo[1,3]dioxole-5-carboxylic acid [4-(2-diethylamino-ethylcarbamoyl)-5-methoxyethoxy-phenyl]-amide; benzo[1,3]dioxole-5-carboxylic acid [4-(2-morpholin-4-yl-ethylcarbamoyl)-5-methoxy-phenyl]-amide; benzo[1,3]dioxole-5-carboxylic acid [4-(2-diisopropylamino-ethylcarbamoyl)-5-methoxy-phenyl]-amide; benzo[1,3]dioxole-5-carboxylic acid [4-(2-dibutylamino-ethylcarbamoyl)-5-methoxy-phenyl]-amide; benzo[1,3]dioxole-5-carboxylic acid [4-(2-thiomorpholin-1-yl-ethylcarbamoyl)-1-methoxy-phenyl]-amide; benzo[1,3]dioxole-5-carboxylic acid [4-(2-piperidin-1-yl-ethylcarbamoyl)-5-methoxy-phenyl]-amide; benzo[1,3]dioxole-5-carboxylic acid [4-(2-pyrrolidin-1-yl-ethylcarbamoyl)-5-methoxy-phenyl]-amide; benzo[1,3] di(methoxy)-5-carboxylic acid [4-(2-diethylamino-ethylcarbamoyl)-5-ethoxy-phenyl]-amide; benzo[1,3] dioxole-5-carboxylic acid [4-(2-diethylamino-ethylcarbamoyl-5-ethoxy-phenyl]-amide; phenylcarboxylic acid [4-(2-diethylamino-ethylcarbamoyl)-5-methoxy-phenyl]-amide; 2-methoxyphenylcarboxylic acid [4-(2-diethylamino-ethylcarbamoyl)-5-methoxy-phenyl]-amide; 3-methoxyphenylcarboxylic acid [4-(2-diethylamino-ethylcarbamoyl)-5-methoxy-phenyl]-amide; 4-methoxyphenylcarboxylic acid [4-(2-diethylamino-ethylcarbamoyl)-5-methoxy-phenyl]-amide; 2-chlorophenylcarboxylic acid [4-(2-diethylamino-ethylcarbamoyl)-5-methoxy-phenyl]-amide; 3-chlorophenylcarboxylic acid [4-(2-diethylamino-ethylcarbamoyl)-5-methoxy-phenyl]-amide; 4-chlorophenylcarboxylic acid [4-(2-diethylamino-ethylcarbamoyl)-5-methoxy-phenyl]-amide; 2-fluorophenylcarboxylic acid [4-(2-diethylamino-ethylcarbamoyl)-5-methoxy-phenyl]-amide; 3-fluorophenylcarboxylic acid [4-(2-diethylamino-ethylcarbamoyl)-5-methoxy-phenyl]-amide; 4-fluorophenylcarboxylic acid [4-(2-diethylamino-ethylcarbamoyl)-5-methoxy-phenyl]-amide; 2,3-dimethoxyphenylcarboxylic acid [4-(2-diethylamino-ethylcarbamoyl)-5-methoxy-phenyl]-amide; 2,4-dimethoxyphenylcarboxylic acid [4-(2-diethylamino-ethylcarbamoyl)-5-methoxy-phenyl]-amide; 2,5-dimethoxyphenylcarboxylic acid [4-(2-diethylamino-ethylcarbamoyl)-5-methoxy-phenyl]-amide; 3,4-dimethoxyphenylcarboxylic acid [4-(2-diethylamino-ethylcarbamoyl)-5-methoxy-phenyl-amide; 3,5-dimethoxyphenylcarboxylic acid [4-(2-diethylaminoethylcarbamoyl)-5-methoxy-phenyl]-amide; 3,4,5-trimethoxyphenylcarboxylic acid [4-(2-diethylamino-ethylcarbamoyl)-5-methoxy-phenyl]-amide.

Example 3

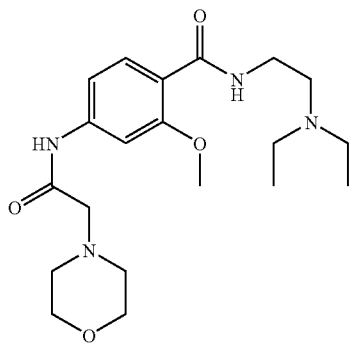

N-(2-Diethylamino-ethyl)-2-methoxy-4-(2-morpholin-4-yl-acetylamino)-benzamide 530 mg (2 mmol) of 4-amino-N-(2-diethylamino-ethyl)-2-methoxy-benzamide is mixed at 4° C. in 24 ml of toluene with 1 ml of trimethylaluminum (2-molar in toluene), and it is stirred for 0.5 hour at room temperature. Then, 320 mg (2 mmol) of methyl-N-morpholinoacetate is added to the batch, and it is heated for 1 hour to 120° C. 50 ml of dilute sodium carbonate solution is then added, and it is extracted three times with 50 ml each of ethyl acetate. The ethyl acetate phase is washed with water, dried, filtered and concentrated by evaporation. The residue is chromatographed on 10 g of Isolute N112 (50 μm) with a gradient from hexane to hexane:methylene chloride=5:95 as an eluant, and 157 mg (20% of theory) of N-(2-diethylamino-ethyl)-2-methoxy-4-(2-morpholin-4-yl-acetylamino)-benzamide is obtained as an oil.

Example 4

N-[4-(2-Diethylamino-ethylcarbamoyl)-3-methoxy-phenyl]-malonic acid tert-butyl ester

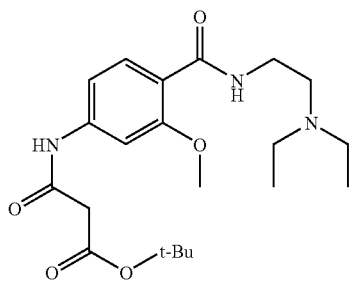

In 16 ml of dimethylformamide (absolute), 530 mg (2 mmol) of 4-amino-N-(2-diethylamino-ethyl)-2-methoxy-benzamide, 320 mg (2 mmol; 0.31 ml) of malonic acid-t-butyl ester, 505 mg (5 mmol; 0.55 ml) of N-methylmorpholine and 912 mg (2.4 mmol) of O-(7-azabenzotriazol-1-yl)-1,1,3,3-tetramethyluronium hexafluorophosphate (HATU) are added in succession, and this batch is stirred for 2 hours at room temperature. The batch is then mixed with water and concentrated by evaporation. The residue is taken up in methylene chloride and suctioned off. The filtrate is concentrated by evaporation and first chromatographed on 10 g of Isolute $NH_2$ (50 μm) with a gradient from methylene chloride to methylene chloride:ethanol=98:2 as an eluant, and 278 mg (34% of theory) of N-[4-(2-diethylamino-ethylcarbamoyl)-3-methoxy-phenyl]-malonic acid tert-butyl ester (melting point: 110° C.) is obtained.

Example 5

N-(2-Diethylamino-ethyl)-4-(2-hydroxy-acetylamino)-2-methoxybenzamide

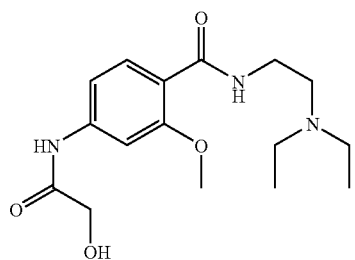

a.) N-(2-Diethylamino-ethyl)-4-(2-benzyloxy-acetylamino)-2-methoxy-benzamide

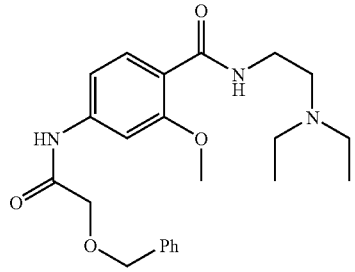

664 mg (4 mmol) of benzyloxyacetic acid is introduced into 20 ml of methylene chloride, mixed with 768 mg (4 mmol) of N'-(3-dimethylaminopropyl)-N-ethylcarbodiimide (EDG), and stirred for 0.5 hour at 4° C. Then, 1.06 g (4 mmol) of 4-amino-N-(2-diethylamino-ethyl)-2-methoxy-benzamide in a total of 12 ml of methylene chloride is added to the batch and stirred for 48 hours at room temperature. After 30 ml of water is added, it is extracted twice with 30 ml each of methylene chloride. The organic phase is dried, filtered and concentrated by evaporation. The residue is chromatographed on 20 g of Isolute $NH_2$ (50 μm) with methylene chloride. The correspondingly combined fractions are concentrated by evaporation and chromatographed again on 20 g of Isolute $NH_2$ (50 μm) with a gradient from cyclohexane to cyclohexane:methylene chloride 50:50 as an eluant, and 348 mg (27% of theory) of N-(2-diethylamino-ethyl)-4-(2-benzyloxy-acetylamino)-2-methoxy-benzamide is obtained as an oil.

Produced basically analogously is: N-(2-diethylamino-ethyl)-4-(3-benzyloxy-propionylamino)-2-methoxy-benzamide.

b.) N-(2-Diethylamino-ethyl)-4-(2-hydroxy-acetylamino)-2-methoxy-benzamide 340 mg (0.82 mmol) of N-(2-diethylamino-ethyl)-4-(2-benzyloxy-acetylamino)-2-methoxy-benzamide is mixed in 40 ml of methanol with 200 mg of palladium on carbon (10%), and it is hydrogenated for 1.5 hours at normal pressure and at room temperature. After the catalyst is drawn off on diatomaceous earth, the filtrate is concentrated by evaporation, and the residue is chromatographed on 10 g of Isolute NH$_2$ (50 µm) with a gradient from methylene chloride. The correspondingly combined fractions are concentrated by evaporation and again on 20 g of Isolute NH$_2$ (50 µm) with a gradient from cyclohexane to cyclohexane:methylene chloride=50:50, and 60 mg (22.6% of theory) of N-(2-diethylamino-ethyl)-4-(2-hydroxy-acetylamino)-2-methoxy-benzamide is obtained as an oil.

Produced analogously is: N-(2-diethylamino-ethyl)-4-(3-hydroxy-propionylamino)-2-methoxy-benzamide.

Example 6

N-(2-Diethylamino-ethyl)-4-(bismethanesulfonylamino)-2-methoxy-benzamide

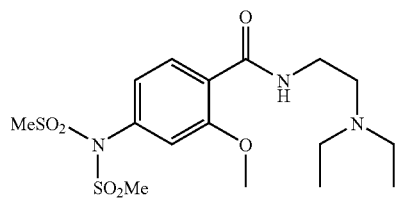

265 mg (1 mmol) of 4-amino-N-(2-diethylamino-ethyl)-2-methoxy-benzamide is introduced into 15 ml of methylene chloride and mixed in succession with 111 mg (1.1 mmol) of triethylamine and 126 mg (1.1 mmol) of methanesulfonic acid chloride. It is stirred for 2 hours at room temperature and then allowed to stand overnight. It is then mixed with 25 ml of saturated sodium bicarbonate solution and shaken out three times with 25 ml each of methylene chloride. The collected organic phase is dried, filtered and concentrated by evaporation. The residue is chromatographed on 10 g of basic silica gel (Isolute flash Si NH$_2$) with a gradient from cyclohexane:ethyl acetate=100:0 to 50:50. 232 mg (52.6% of theory) of N-(2-diethylamino-ethyl)-4-(bismethanesulfonylamino)-2-dimethoxy-benzamide with a melting point of 144.1° C. is obtained.

Example 7

N-(2-Diethylamino-ethyl)-4-(methanesulfonylamino)-2-methoxy-benzamide

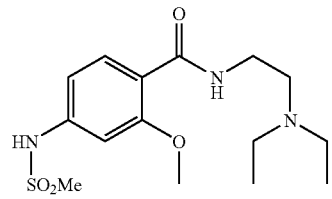

150 mg (0.36 mmol) of N-(2-diethylamino-ethyl)-4-(bismethanesulfonylamino)-2-methoxy-benzamide is dissolved in 10 ml of tetrahydrofuran and mixed with 1 ml of 1N potassium hydroxide solution. It is stirred for 2 hours at room temperature. Then, the tetrahydrofuran is drawn off in a vacuum, mixed with 25 ml of saturated sodium bicarbonate solution and shaken out three times with 25 ml each of methylene chloride. The collected organic phase is dried, filtered and concentrated by evaporation, and 114 mg (91.9% of theory) of N-(2-diethylamino-ethyl)-4-(methanesulfonylamino)-2-methoxy-benzamide is obtained.

Example 8

[2-(4-Acetylamino-2-methoxy-benzoylamino)-ethyl]-diethyl-methyl-ammonium iodide

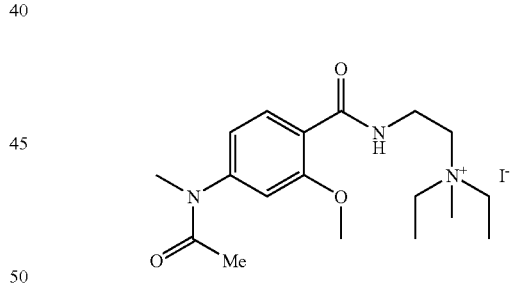

307 mg (1 mmol) of 4-acetylamino-N-(2-diethylamino-ethyl)-2-methoxy-benzamide is mixed in 8 ml of dimethylformamide with 358 mg (1.1 mmol) of cesium carbonate and 312 mg (2.2 mmol) of iodomethane, and it is heated under argon in a pressure vessel for 2.5 hours to a bath temperature of 80° C. After concentration by evaporation under vacuum, it is taken up in 25 ml of saturated sodium bicarbonate solution and extracted three times with 25 ml each of methylene chloride. The collected organic phase is dried, filtered and concentrated by evaporation, and 145 mg (32% of theory) of [2-(4-acetylamino-2-methoxy-benzoylamino)-ethyl]-diethyl-methyl-ammonium iodide with a melting point >300° C. is obtained.

Example 9

Benzo[1,3]dioxole-5-carboxylic acid [4-(2-diethylamino-ethylcarbamoyl)-2-iodo-5-methoxy-phenyl]-amide

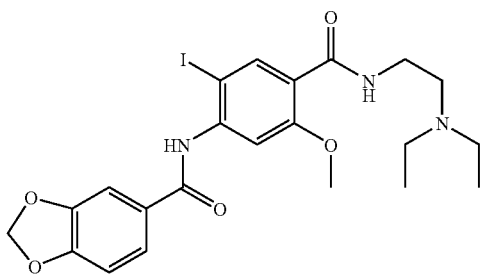

Synthesis with I-127 (not radioactive): 100 mg (corresponding to 0.242 mmol) of benzo[1,3]dioxole-5-carboxylic acid [4-(2-diethylamino-ethylcarbamoyl)-5-methoxy-phenyl]-amide (from Example 2) was dissolved under $N_2$ at room temperature in 5 ml of trifluoroacetic acid (TFA). 157 mg (corresponding to 0.290 mmol) of thallium-(III)-TFA; (Tl (TFA)$_3$) salt was added in solid form to the light-yellow, clear starting solution. After 10 minutes, 38.8 mg (corresponding to 0.259 mmol) of sodium iodide ([1-127]NaI), dissolved in a little $H_2O$, was added. Then, the batch was stirred overnight at room temperature. Then, the TFA was drawn off under high vacuum (H.V.) until a dry state was reached, and the orange-brown, oily residue was dried for 2 more hours under H.V. This residue was taken up in 3 ml of $CH_2Cl_2$ and extracted with 3×1 ml of saturated $NaHCO_3$ solution and 1×1 ml of $H_2O$. The combined aqueous phases were reextracted with 3×1 ml of ethyl acetate. The combined organic phases were dried on $MgSO_4$ and dried overnight under H.V. after spinning-in. Purification of the compound was carried out via column chromatography on silica gel (Mesh 60), mobile solvent: 200 ml of $CH_2$—$Cl_2$MeOH, 97:3; 200 ml of $CH_2Cl_2$/MeOH, 95:5, 300 ml of $CH_2Cl_2$/MeOH, 8:2. Yield: 113 mg, corresponding to 86%.

Synthesis with I-123; I-125; I-131: 20 μl (corresponding to 0.200 μmol) of benzo[1,3]dioxole-5-carboxylic acid [4-(2-diethylamino-ethylcarbamoyl)-5-methoxy-phenyl]-amide (from Example 2) in trifluoroacetic acid (TFA) and 25 μl of Tl(TFA)$_3$ (0.250 μmol) in TFA were combined and incubated for 5 minutes at room temperature. After 10 μl of [I-123 or I-125 or I-131]NaI solution (in NaOH (0.1 M)) was added, the TFA and the sodium hydroxide solution were removed in a nitrogen stream. The dry mixture was taken up in 50 μl of MeCl$_2$/MeOH (95/5), and any Tl residues were removed on an RP cartridge. The solvent mixture was removed in a nitrogen stream, and the remaining residue was taken up again in ethanol/phosphate-buffered common salt solution (PBS, 0.1 M, pH 7.4) (5/95) and passed trough a 0.45 μm filter.

Produced analogously are: N-(2-diethylamino-ethyl)-5-iodo-2-methoxy-4-propionylylamino-benzamide; N-(2-diethylamino-ethyl)-4-(2,2-dimethyl-propionylamino)-5-iodo-2-methoxy-benzamide; N-(2-diethylamino-ethyl)-4-(2-hydroxy-acetylamino)-5-iodo-2-methoxy-benzamide; N-(2-diethylamino-ethyl)-4-(3-hydroxy-propionylamino)-5-iodo-2-methoxy-benzamide; N-(2-diethylamino-ethyl)-4-{2-[(2-hydroxy-ethyl)-methyl-amino]-acetylamino}-5-iodo-2-methoxy-benzamide; N-(2-diethylamino-ethyl)-5-iodo-2-methoxy-4-(2-morpholin-4-yl-acetylamino)-benzamide; 4-hydroxy-1-methyl-pyrrolidine-2-carboxylic acid [4-(2-diethylamino-ethylcarbamoyl)-2-iodo-5-methoxy-phenyl]-amide; N-(2-diethylamino-ethyl)-5-iodo-4-methanesulfonylamino-2-methoxy-benzamide; N-(2-diethylamino-ethyl)-5-iodo-4-butanesulfonylamino-2-methoxy-benzamide; N-(2-diethylamino-ethyl)-4-carboxy-acetylamino-5-iodo-2-methoxy-benzamide.

The compounds according to the invention can also be purified by reversed-phase-high-pressure liquid chromatography. The specific radioactivity of such a purified compound will be higher than the specific radioactivity for the unpurified compound.

Mouse Model Studies

After synthesis and purification, the compounds according to the invention are dissolved in a physiologically compatible medium and kept ready for injection. Organ distribution and tumor accumulation experiments were performed in B16/F1 tumor-bearing C57BL6 mice, and SK-Mel-3 tumor-bearing NMRI nude mice (15-22 g).

Murine B16/F1 and human SK-Mel-3 cells were ordered from ATCC. B16/F1 cells (0.5×10$^6$) are washed in buffer (preferably phosphate buffer), suspended and inoculated subcutaneously into C57BL6 mice, 100 μl, in the right rear flanks. Sk-Mel-3 cells (5×10$^6$) are washed in buffer and then inoculated subcutaneously into NMRI mice in Matrigel® (100 μl) in the right side of the trunk. After about 8-10 days, the animals develop palpable tumors with a surface area of about 30 mm$^2$. The distribution studies are performed after intravenous caudal vein administration of 3.7-5.5 MBq of the substances according to the invention in 50-100 μl of volume. At certain times after administration, the animals are sacrificed, organs and tumors are removed, optionally dabbed dry, weighed and measured for radioactive content (γ measurement) in a calibrator with the corresponding isotope standard. The results are depicted as % of the injected dose (ID)/g of tissue (Table 1).

The entire disclosures of all applications, patents and publications, cited herein and of corresponding German application No. 102004011720.9-41, filed Mar. 10, 2004 and U.S. Provisional Application Ser. No. 60/551,356, filed Mar. 10, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for the diagnosis and/or treatment of a tumor melanoma, comprising administering to a subject in need thereof an effective amount of a radiohalogenated compound of formula (I),

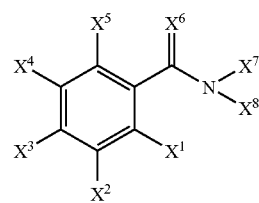

in which
X¹ is an ether of formula —O—R³,
X³ is a radical of formula —NR¹R²,
X², X⁴ and X⁵ are, independently of one another, a halogen, hydrogen, a radical of formula —NR¹R², an ether of formula —O—R³, a branched or unbranched $C_1$—$C_{10}$ alkyl group, a branched or unbranched $C_2$—$C_{10}$ alkenyl group or an aryl or heteroaryl group that is optionally substituted by halogen or low alkoxy,
wherein two adjacent radicals X¹ to X⁵ may form a 5- to 7-membered ring, wherein one or more carbon atoms of the ring are optionally replaced by heteroatoms,
X⁶ is an oxygen or —NH—,
X⁷ and X⁸ are the same or different and are hydrogen, $C_{1-12}$ alkyl, $C_{2-12}$ alkenyl, $C_{3-6}$ cycloalkyl, $C_{3-6}$ cycloalkenyl, $C_{2-6}$ carbalkoxyalkyl, $C_{2-6}$ carbalkoxyalkenyl, $C_{6-12}$ aryl or $C_{6-12}$ heteroaryl; in each case optionally substituted in one or more places by OR⁴, COOR⁵, CONR⁶R⁷, cyano, halogen or NR⁸R⁹,
or
X⁷ and X⁸ together form a 5- to 7-membered ring, wherein one or more carbons of the ring are optionally replaced by heteroatoms,
R¹ and R² are the same or different and are hydrogen, $C_{1-12}$ alkyl, $C_{2-12}$ alkenyl, $C_{3-6}$ cycloalkyl, $C_{3-6}$ cycloalkenyl, $C_{2-6}$ carboxyalkyl, $C_{2-6}$ carboxyalkenyl, $C_{1-12}$ alkyl, $C_{6-12}$ arylsulfonyl, carboxyaryl, carboxy heteroaryl; in each case optionally substituted in one or more places by aryl, heteroaryl, OR⁴, COOR⁵, CONR⁶R⁷, cyano, halogen or NR⁸R⁹, or two substituents taken together form a 3, 4, 5, 6, 7 or 8 membered ring, optionally with 1, 2, 3, or 4 hetero atoms,
R³ is hydrogen, $C_{6-12}$ aryl, heteroaryl, $C_{1-10}$ alkyl, $C_{2-10}$ alkenyl, $C_{2-10}$ alkinyl, $C_{3-6}$ cycloalkyl, $C_{3-6}$ cycloalkenyl, in each case optionally substituted in one or more places by OR⁴, COOR⁵, CONR⁶R⁷, cyano, halogen or NR⁸R⁹,
R⁴ and R⁵ are the same or different and are hydrogen, $C_{1-12}$ alkyl, $C_{2-12}$ alkenyl, $C_{3-6}$ cycloalkyl, $C_{3-6}$ cycloalkenyl, optionally substituted in one or more places by aryl, heteroaryl, OR¹⁰, COOR¹¹, CONR⁶R⁷, cyano, halogen or NR⁸R⁹,
R⁶, R⁷, R⁸ and R⁹ are the same or different and are hydrogen, $C_{1-12}$ alkyl, $C_{2-12}$ alkenyl, $C_{3-6}$ cycloalkyl, $C_{3-6}$ cycloalkenyl, in each case optionally substituted in one or more places by OR⁴, or R⁶ and R⁷ or R⁸ and R⁹ in each case together form a 5- to 7-membered ring, wherein one or more carbons of the ring are optionally replaced by heteroatoms, and
R¹⁰ and R¹¹ are the same or different and are hydrogen, $C_{1-12}$ alkyl, $C_{2-12}$ alkenyl, $C_{3-6}$ cycloalkyl, $C_{3-6}$ cycloalkenyl, which are optionally substituted in each case in one or more places by aryl, heteroaryl, OR⁴, COOR⁵, CONR⁶R⁷, cyano, halogen, or NR⁸R⁹,
provided that
R¹ and R² cannot simultaneously be hydrogen,
at least one of radicals X², X⁴ and X⁵ is a radioactive halogen,
at least one of radicals X², X³, X⁴ and X⁵ is a radical of formula —NR¹R², in which either R¹ or R² is a substituted or unsubstituted radical carboxyalkyl, carboxyalkenyl carboxyaryl or carboxyheteroaryl, and
with the proviso that if X¹ is methoxy and X⁶ is oxygen, X⁸ is hydrogen and X⁷ is NH(CH₂)₂NEt₂, and X⁴ is I¹³¹, X³ is not NHAc, or a pharmaceutically acceptable salt thereof.

2. The method of claim 1 in which the compound of formula I has an alkoxy substituent in the ortho-position of the benzene ring.

3. The method of claim 2 in which the compound of formula I has a halogen substituent in the meta-position of the benzene ring.

4. The method of claim 3 in which the compound of formula I exhibits lower blood accumulation, better liver kinetics, lower thyroid gland accumulation from released iodine, extended retardation in melanoma tissue, and faster excretion from the liver relative to a radiohalogenated benzamide derivative having an amino substituent in the para-position of the benzene ring, which amino substituent bears a carboxy alkyl group with formation of an amide bond.

5. The method of claim 3 in which the ratio of tumor to blood concentration of the compound of formula I 5 hours after administration is at least 25:1.

6. The method of claim 5, in which the ratio of tumor to liver concentration of the compound of formula I 5 hours after administration is at least 3.4:1.

7. The method of claim 3 in which the tumor to blood concentration of the compound of formula I 24 hours after administration is at least 375:1.

8. The method of claim 7 in which the ratio of tumor to liver concentration of the compound of formula I 24 hours after administration is at least 38:1.

9. The method of claim 3 in which the ratio of tumor to blood concentration of the compound of formula I 24 hours after administration is at least 450:1.

10. The method of claim 9 in which the ratio of tumor to liver concentration of the compound of formula I 24 hours after administration is at least 40:1.

11. The method of claim 3 in which the carboxyaryl comprises a carboxyphenyl.

12. The method of claim 11, wherein the carboxyphenyl is substituted by a fluorine atom.

13. The method according to claim 3, wherein the compound of formula I is compound e (BA 100)

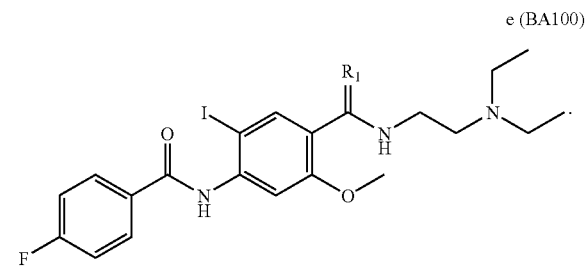

e (BA100)

14. The method according to claim 13, wherein the ratio of tumor to blood concentration of compound e (BA 100) 6 hours after administration is 40:1.

15. The method according to claim 13, wherein the ratio of tumor to liver concentration of compound e (BA 100) 6 hours after administration is 6:1.

16. The method according to claim 13, wherein the ratio of tumor to blood concentration of compound e (BA 100) 24 hours after administration is 452:1.

17. The method according to claim 13, wherein the ratio of tumor to liver concentration of benzamide compound e (BA 100) 24 hours after administration is 41:1.

18. The method according to claim 1, wherein the radioactive halogen is F-18, Br-75, I-123, I-124, I-125, I-131 or At-211.

19. The method according to claim 1, wherein the radioactive halogen is F-18, Br-76, I-123, I-124, I-125, I-131 or At-211.

* * * * *